United States Patent
Furui et al.

(10) Patent No.: US 6,197,953 B1
(45) Date of Patent: Mar. 6, 2001

(54) PROCESS FOR PREPARING OPTICALLY ACTIVE TRANS-3-SUBSTITUTED GLYCIDIC ACID ESTER

(75) Inventors: Masakatsu Furui, Takatsuk; Toshiyuki Furutani, Sanda, both of (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 0 days.

(21) Appl. No.: 09/293,178

(22) Filed: Apr. 16, 1999

Related U.S. Application Data

(62) Division of application No. 09/032,030, filed on Feb. 27, 1998, now Pat. No. 5,998,637.

(30) Foreign Application Priority Data

Feb. 27, 1997 (JP) .................................................. 9-43378
Dec. 11, 1997 (JP) .................................................. 9-341668

(51) Int. Cl.$^7$ ................................................ C07D 281/10
(52) U.S. Cl. ........................................ 540/491; 540/544
(58) Field of Search ........................... 540/491, 544

(56) References Cited

U.S. PATENT DOCUMENTS

| | | | |
|---|---|---|---|
| 3,562,257 | 2/1971 | Kugita et al. | 540/491 |
| 4,566,995 | 1/1986 | Simonovitch et al. | 540/491 |
| 4,908,469 | 3/1990 | Martin | 560/17 |
| 4,937,334 | 6/1990 | Cavicchioli et al. | 540/491 |
| 5,008,411 | 4/1991 | Coffen et al. | 540/491 |
| 5,223,612 | 6/1993 | Giordano et al. | 540/491 |
| 5,495,013 | 2/1996 | Piselli et al. | 540/491 |
| 5,663,332 | 9/1997 | Hytönen | 540/491 |

FOREIGN PATENT DOCUMENTS

| | | |
|---|---|---|
| 657544A1 | 10/1989 | (EP) . |
| 417785A1 | 3/1991 | (EP) . |
| 453330A1 | 10/1991 | (EP) . |
| 0343714B1 | 11/1994 | (EP) . |
| 0362556B1 | 11/1994 | (EP) . |
| 2246351 | 1/1992 | (GB) . |
| 2247020 | 2/1992 | (GB) . |
| 41-5447 | 3/1966 | (JP) . |
| 46-8982 | 3/1971 | (JP) . |
| 50-24954 | 8/1975 | (JP) . |
| 53-18038 | 6/1978 | (JP) . |
| 58-99471 | 6/1983 | (JP) . |
| 60-13776 | 1/1985 | (JP) . |
| 60-202871 | 10/1985 | (JP) . |
| 61-18549 | 5/1986 | (JP) . |
| 61-145174 | 7/1986 | (JP) . |
| 61-268663 | 11/1986 | (JP) . |
| 61-52142 | 11/1986 | (JP) . |
| 63-13994 | 3/1988 | (JP) . |
| 63-51148 | 10/1988 | (JP) . |
| 2-17169 | 1/1990 | (JP) . |
| 2-28594 | 6/1990 | (JP) . |
| 2-231480 | 9/1990 | (JP) . |
| 2-286672 | 11/1990 | (JP) . |
| 2-289558 | 11/1990 | (JP) . |
| 3-175995 | 7/1991 | (JP) . |
| 4-217969 | 8/1992 | (JP) . |
| 4-221376 | 8/1992 | (JP) . |
| 4-234866 | 8/1992 | (JP) . |
| 5-201865 | 8/1993 | (JP) . |
| 5-202013 | 8/1993 | (JP) . |

(List continued on next page.)

OTHER PUBLICATIONS

*Enantiomers, Racemates and Resolutions*, Jacques et al., John Wiley & Sons, pp. 223–250 (1981).

(List continued on next page.)

*Primary Examiner*—Ba K. Trinh
(74) *Attorney, Agent, or Firm*—Birch, Stewart, Kolasch & Birch, LLP

(57) ABSTRACT

Methods for the preparation of (2S,3S)-1,5-benzothiazepine derivatives of the formula (II) and isomers thereof, and for the preparation of (2R,3R)-1,5-benzothiazepine derivatives of the formula (III) and isomers thereof,

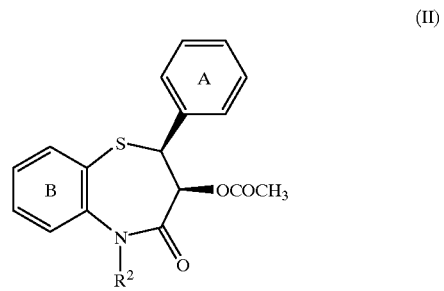

(II)

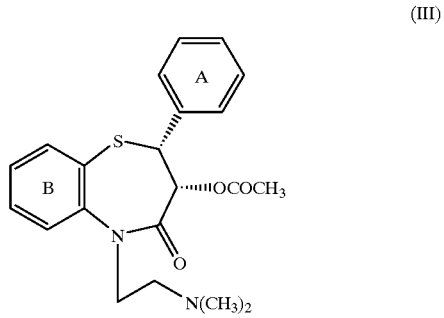

(III)

wherein ring A and ring B are independently a substituted or unsubstituted benzene ring, and $R^2$ is a 2-(dimethylamino) ethyl group or a group of the formula:

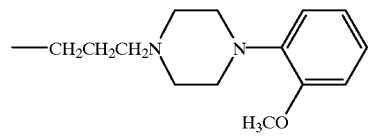

or a pharmaceutically acceptable salt thereof.

35 Claims, 1 Drawing Sheet

FOREIGN PATENT DOCUMENTS

| | | |
|---|---|---|
| 5-301864 | 11/1993 | (JP) . |
| 6-78790 | 3/1994 | (JP) . |
| 6-279398 | 10/1994 | (JP) . |
| 8-259552 | 10/1996 | (JP) . |
| WO89/02428 | 3/1989 | (WO) . |
| WO89/10350 | 11/1989 | (WO) . |
| WO90/04643 | 5/1990 | (WO) . |

OTHER PUBLICATIONS

*Optical Resolution by Preferential Crystallization and Replacing Crystallization of DL–Allothreonine*, Bull. Chem. Soc. Jpn., 67, pp. 1899–1903 (1994).

*Nature*, vol. 205, pp. 590–591, (1965).

*Synthesis of 1,5 Benzothiazepine Derivatives*, Chem. Phar. Bull., 18(10) pp. 2028–2037 (1970).

J. A. Vega et al., Tetrahedron Letters, 37(35):6413–6416 (1996).

*Synthetic Communications*, vol. 19 (1&2), pp. 221–232 (1989).

*Biocatalysis and Biotransformation*, vol. 22, pp. 205–214 (1995).

PROCESS FOR PREPARING OPTICALLY ACTIVE TRANS-3-SUBSTITUTED GLYCIDIC ACID ESTER

This application is a divisional of application Ser. No. 09/032,030, filed on Feb. 27, 1998, now U.S. Pat. No. 5,998,637 the entire contents of which are hereby incorporated by reference.

BACKGROUND OF THE INVENTION

The present invention relates to a process for preparing optically active trans-3-substituted glycidic acid esters. More particularly, the present invention relates to a process for preparing optical isomers of trans-3-(substituted or unsubstituted phenyl)glycidic acid esters which are useful as intermediates for the synthesis of pharmaceutical compounds, and the use of the optical isomers.

Diltiazem hydrochloride, the chemical name of which is (2S, 3S)-3-acetoxy-5-[2-(dimethylamino)ethyl]-2,3-dihydro-2-(4-methoxyphenyl)-1,5-benzothiazepin-4 (5H)-one hydrochloride, is a pharmaceutical compound widely used as a calcium channel blocker for the treatment of angina pectoris, essential hypertension and the like (Merck Index, XII Ed., page 541).

For the preparation of diltiazem, conventionally known is a process wherein racemic trans-3-(4-methoxyphenyl) glycidic acid ester is used as the starting material and an optical resolution is carried out at a later stage in the synthesis, as disclosed in Japanese Patent Publication Kokoku No. 46-16749, No. 53-18038 and No. 61-52142.

Also, a process using a (2R,3S)-3-(4-methoxyphenyl) glycidic acid methyl ester obtained by optical resolution of the racemic trans-glycidic acid ester is proposed for the preparation of diltiazem in apanese Patent Publication Kokai No. 60-13776.

Thus, various processes for the preparation of optically active trans-3-(4-methoxyphenyl)glycidic acid esters have been investigated and, for instance, processes as mentioned below are proposed:

(a) a process comprising hydrolyzing racemic trans-3-(4-methoxyphenyl)glycidic acid methyl ester to form an alkali metal salt, forming its diastereomeric salt with an optically resolving reagent such as (−)-α-methylbenzylamine, resolving the salt and esterifying again the obtained optically active salt (Japanese Patent Publication Kokai No. 61-145174 and No. 2-231480), b) a process comprising conducting a Darzens reaction of a chloroacetic acid ester having an asymmetric ester residue such as (−)-menthyl group, (−)-2-phenylcyclohexyl group or (−)-8-phenylmenthyl group with p-anisaldehyde (Japanese Patent Publication Kokai No. 61-268663, No. 2-17170 and No. 2-17169), (c) a process comprising enzymatically and asymmetrically hydrolyzing (2S, 3R)-isomer in racemic trans-3-(4-methoxyphenyl)glycidic acid methyl ester and recovering the remaining (2R,3S)-isomer (Japanese Patent Publication Kokai No. 2-109995 and No. 3-15398 and WO 90/04643), (d) a process for the asymmetric synthesis of (2R, 3S)-3-(4-methoxyphenyl)glycidic acid methyl ester comprising subjecting trans-4-methoxycinnamic acid methyl ester to osmium oxidation in the presence of an asymmetric catalyst to give an optically active diol and subjecting the diol to intramolecular ring closure to give the desired compound (WO 89/02428 and WO 89/10350), and (e) a process comprising subjecting (2S, 3R)-isomer in racemic trans-3-(4-methoxy-phenyl)glycidic acid methyl ester to enzymatic asymmetric transesterification with butanol to give (2R, 3S)-3-(4-methoxyphenyl)glycidic acid methyl ester (Japanese Patent Publication Kokai No. 4-228095 and No. 6-78790).

It is also known that some 1,5-benzothiazepine derivatives other than diltiazem have excellent pharmacological activities. For instance, Japanese Patent Publication Kokai No. 60-202871 discloses that benzothiazepine derivatives having a reverse absolute configuration of diltiazem at the 2- and 3-positions have platelet aggregation inhibitory activity and the like.

It is also known that (2S,3R)-3-(4-methylphenyl)glycidic acid methyl ester which is useful in the synthesis of this derivative is prepared by enzymatic asymmetric hydrolysis of racemic trans-3-(4-methylphenyl)glycidic acid methyl ester (Japanese Patent Publication Kokai No. 3-175995).

Japanese Patent Publication Kokai No. 8-259552 discloses a process for obtaining both isomers of trans-3-(4-methoxyphenyl)glycidic acid methyl ester in high optical purity from racemate by enzymatically and asymmetrically transesterifying the (2S, 3R)-isomer therein with butanol, recovering the untransesterified (2R, 3S)-3-(4-methoxyphenyl)glycidic acid methyl ester and chemically transesterifying the transesterified product, i.e., (2S,3R)-3-(4-methoxyphenyl)glycidic acid butyl ester to convert into the corresponding methyl ester.

Japanese Patent Publication Kokai No. 4-217969 discloses a process for obtaining crystals of (2R, 3S)-isomer of trans-3-(4-methoxyphenyl)glycidic acid methyl ester by dissolving an equimolar mixture of (2R,3S)-isomer and (2S, 3R)-isomer and (2R,3S)-isomer in t-butyl methyl ether solvent under heating, adding a crystalline seed of (2R,3S)-isomer, and crystallizing (2R,3S)-isomer, thereby giving crystalline (2R,3S)-isomer in an amount slightly larger than that of (2R, 3S)-isomer initially dissolved together with the equimolar mixture.

Also, Japanese Patent Publication Kokai No. 5-301864 discloses a process for obtaining crystals of (2R, 3S)-isomer of trans-3-(4-methoxyphenyl)glycidic acid 4-chloro-3-methylphenyl ester by thermally dissolving an equimolar mixture of (2R, 3S)-isomer and (2S, 3R)-isomer, and the (2R, 3S)-isomer in tetrahydrofuran, adding a crystalline seed of (2R, 3S)-isomer, and crystallizing (2R,3S)-isomer at 30° C., thereby giving crystalline (2R,3S)-isomer in an amount slightly larger than that of (2R,3S)-isomer initially dissolved together with the equimolar mixture.

Further, Japanese Patent Publication Kokai No. 8-259552 discloses a process for obtaining (2R,3S)-isomer of trans-3-(4-methoxyphenyl)glycidic acid methyl ester from an equimolar mixture of (2R, 3S)-isomer and (2S, 3R)-isomer by enzymatically and asymmetrically transesterifying the (2S, 3R)-isomer therein with butanol until the molar ratio of (2S, 3R)-butyl ester/(2S,3R)-methyl ester is 7.8/1, and crystallizing the (2R, 3S)-isomer therefrom.

However, in this process, in order to prevent the contamination in the desired (2R, 3S)-methyl ester due to the crystallization of the unesterified (2S, 3R)-methyl ester remaining in a small amount, the crystallization was stopped in a stage that the (2R,3S)-3-(4-methoxyphenyl)glycidic acid methyl ester still remains in the mother liquor in an amount larger than the untransesterified (2S,3R)-isomer.

Thus, despite the fact that (2R,3S)-3-(4-methoxyphenyl) glycidic acid methyl ester is scarcely transesterified in this transesterification reaction and the transesterification conversion rate of the (2S, 3R)-isomer is high, the yield of (2R,3S)-3-(4-methoxyphenyl)glycidic acid methyl ester obtained in the form of crystals is not satisfactory.

It is an object of the present invention to provide a process for optically resolving trans-3-(substituted or unsubstituted phenyl)glycidic acid esters in a simple manner in a high yield and in high optical purity.

A further object of the present invention is to provide a process for crystallizing a desired optical isomer of trans-3-(substituted or unsubstituted phenyl)glycidic acid ester from a solution containing a mixture of optical isomers thereof in high purity and in a high yield since the desired optical isomer can be crystallized up to the extent that the concentration of the desired optical isomer remaining in the mother liquor is extremely low as compared with known processes.

A still further object of the present invention is to provide a process for crystallizing a desired optical isomer of trans-3-(substituted or unsubstituted phenyl)glycidic acid ester in high purity from a reaction mixture of an enzymatic asymmetric transesterification of racemate up to the extent that the concentration of the desired optical isomer remaining in the mother liquor is extremely low as compared with known processes.

These and other objects of the present invention will become apparent from the description hereinafter.

SUMMARY OF THE INVENTION

It is found by the inventors of the present invention that if, in a solution containing a racemic trans-3-(substituted or unsubstituted phenyl)glycidic acid ester, and an ester compound which is different from one isomer of the racemic ester only in the ester residue and which has a higher solubility than the isomers of the trans-3-(substituted or unsubstituted phenyl)glycidic acid ester, crystallization of an isomer having the same absolute configuration as the ester compound is hindered.

Thus, in accordance with the present invention, there is provided a process for preparing an optically active isomer of trans-3-substituted glycidic acid ester compound of the formula (I):

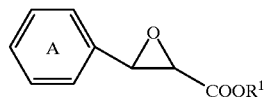

(I)

wherein ring A is a substituted or unsubstituted benzene ring, and $R^1$ is an ester residue, which comprises:

preparing a solution of one optical isomer (A) and the other optical isomer (B) of the ester compound (I), both of which are the optical isomers due to the asymmetric carbons at 2- and 3-positions, and an ester compound (B') which is different from the isomer (B) only in the ester residue $R^1$, crystallizing the optical isomer (A) from the solution up to the extent that the optical isomer (A) is crystallized without the precipitation of the optical isomer (B) due to the presence of the ester compound (B') though the optical isomer (B) would precipitate if the ester compound (B') were not present, and isolating the crystals of the optical isomer (A).

The solution from which the optical isomer (A) is crystallized may further contain a small amount of an ester compound (A') which is different from the optical isomer (A) only in the ester residue $R^1$ and has the same ester residue as the ester compound (B').

The solution from which the optical isomer (A) is crystallized may be a solution obtained by subjecting a solution of the optical isomers (A) and (B) and an alcohol to transesterification in the presence of an enzyme having a stereoselective transesterification ability to transesterify the isomer (B) with the alcohol, thereby producing the ester compound (B').

Thus, the present invention also provides a process for preparing an optically active isomer of trans-3-substituted glycidic acid ester compound of the formula (I):

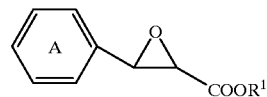

(I)

wherein ring A is a substituted or unsubstituted benzene ring, and $R^1$ is an ester residue, which comprises:

subjecting a mixture of one optical isomer (A) and the other optical isomer (B) of the ester compound (I), both of which are the optical isomers due to the asymmetric carbons at 2- and 3-positions, to transesterification in the presence of an alcohol and an enzyme having a stereoselective transesterification ability, thereby transesterifying the optical isomer (B) with the alcohol to produce an ester compound (B') which is different from the isomer (B) only in the ester residue $R^1$ until the molar ratio of ester compound (B')/isomer (B) falls within the range of 13/7 to 7.8/1, crystallizing the optical isomer (A) from the resulting solution containing the isomer (A), the untransesterified isomer (B) and the ester compound (B'), and isolating the isomer (A) having optical purity of at least 99% in a yield of at least 75% based on the initial amount of optical isomer (A).

The other optical isomer (B) can also be obtained in high purity and in a high yield by, after isolating the isomer (A), chemically transesterifying the ester compound (B') in the mother liquor to convert into the isomer (B) and crystallizing the isomer (B) followed by isolation thereof.

According to the present invention, an optical isomer of trans-3-substituted glycidic acid ester (I) can be crystallized and obtained in high purity from a solution of a mixture of optical isomers of the ester (I) and an ester compound which is different from one of the isomers only in the ester residue, up to the extent that the concentration of the desired optical isomer in the mother liquor becomes very low as compared with that in conventional processes.

Further, from a racemic trans-3-substituted glycidic acid ester, the desired isomer of high purity can be obtained in a simple manner in a high yield by conducting enzymatic asymmetric transesterification of the racemic ester and subsequently crystallizing the desired isomer from the resulting reaction mixture.

Figure 1:
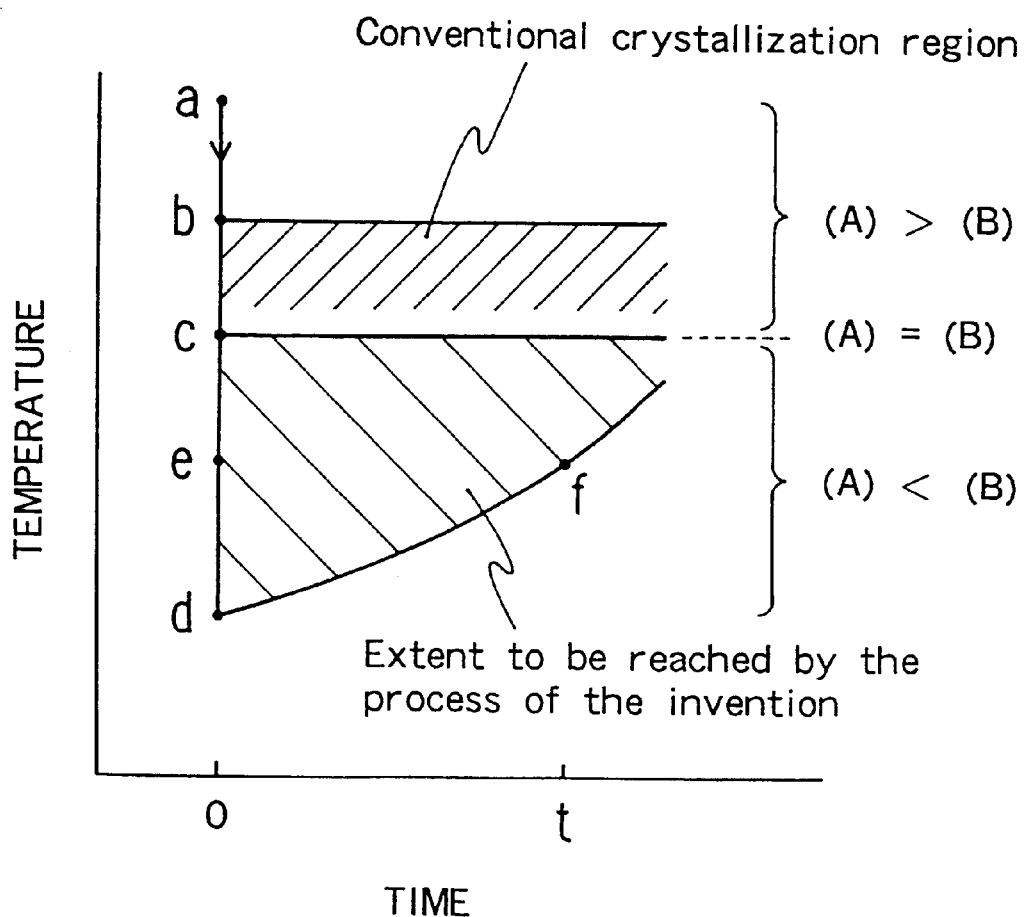
FIG. 1 illustrates the condition under which an optical isomer (A) is crystallized from a solution (a) containing the optical isomers (A) and (B) and an ester compound (B'), but the optical isomer (B) does not precipitate due to the presence of the ester compound (B') though the optical isomer (B) would precipitate in the absence of the ester compound (B') by the use of the parameters of temperature and time.

In this connection, it is assumed that the ratio of the optical isomers (A) and (B) and the ester compound (B') in such solution (a) is sufficient for the inhibition of the crystallization of the optical isomer (B).

DETAILED DESCRIPTION

In the present invention, a solution wherein one optical isomer (A) and the other optical isomer (B) of a trans-3-substituted glycidic acid ester of the formula (I):

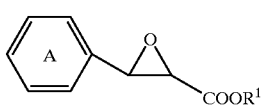

(I)

in which ring A is a substituted or unsubstituted benzene ring and $R^1$ is an ester residue, both of which are the optical isomers due to the asymmetric carbons at the 2- and 3-positions of the ester (I), and an ester compound (B') which is different from the optical isomer (B) only in the ester residue are dissolved in a solvent (hereinafter referred to as "solution ABB'") is used in crystallization.

The solution of the isomers (A) and (B) and the ester compound (B') may further contain a small amount of an ester compound (A') which is different from the isomer (A) only in the ester residue $R^1$ and has the same ester residue $R^1$ as the ester compound (B') (hereinafter referred to as "solution AA'BB'").

The trans-3-substituted glycidic acid esters (I), namely a mixture of the optical isomers (A) and (B) thereof, used in the present invention are the compounds of the formula (I) wherein the ring A is a substituted or unsubstituted benzene ring and $R^1$ is an ester residue which enables to crystallize the trans-3-substituted glycidic acid esters (I) in a solvent for the crystallization.

Such trans-3-substituted glycidic acid esters are, for instance, compounds of the formula (I) wherein the ring A is phenyl group which may be substituted by
(a) a linear or branched lower alkyl group, e.g., methyl group, ethyl group, propyl group, isopropyl group, n-butyl group, sec-butyl group, t-butyl group, n-hexyl group, 2-hexyl group or 3-hexyl group;
(b) a linear or branched lower alkoxy group, e.g., methoxy group, ethoxy group, propyloxy group, isopropyloxy group, n-butoxy group, sec-butoxy group, t-butoxy group, n-hexyloxy group, 2-hexyloxy group or 3-hexyloxy group; or
(c) a halogen atom, e.g., fluorine atom, chlorine atom, bromine atom or iodine atom, and $R^1$ is
(a) a linear or branched lower alkyl group, e.g., methyl group, ethyl group, propyl group, isopropyl group, n-butyl group, sec-butyl group, t-butyl group, n-hexyl group, 2-hexyl group or 3-hexyl group;
(b) a substituted cycloalkyl group, e.g., 2-phenyl-cycloalkyl group; or
(c) a substituted or unsubstituted aryl group, e.g., 4-chloro-3-methylphenyl group.

Preferable examples of the trans-3-substituted glycidic acid ester (I) are, for instance, compounds of the formula (I) wherein the ring A is methylphenyl group or methoxyphenyl group and $R^1$ is methyl group, ethyl group, 2-phenylcyclohexyl group or 4-chloro-3-methylphenyl group. In particular, the compounds of the formula (I) wherein the ring A is 4-methylphenyl group or 4-methoxyphenyl group and $R^1$ is methyl group or ethyl group are the more preferred examples.

Any ester residue may be used for the ester residue of the ester compound (B') so long as it gives the ester compound (B') a good solubility in the solvent used in the crystallization.

The ester residues of the ester compound (B') are, for instance,
(a) a linear or branched alkyl group which may have a substituent and which has more carbon atoms than that of the ester residue $R^1$ of an optical isomer (B), e.g., propyl group, isopropyl group, n-butyl group, sec-butyl group, t-butyl group, n-pentyl group, 2-pentyl group, 3-pentyl group, n-hexyl group, 2-hexyl group, 3-hexyl group, n-heptyl group, 2-heptyl group, 3-heptyl group, 4-heptyl group, n-octyl group, 2-octyl group, 3-octyl group, 4-octyl group, n-nonyl group, 2-nonyl group, 3-nonyl group, 4-nonyl group, 5-nonyl group, n-decyl group, 2-decyl group, 3-decyl group, 4-decyl group or 5-decyl group;
(b) an alkoxyalkyl group which may have a substituent, e.g., methoxymethyl group, ethoxymethyl group, propyloxymethyl group, methoxyethyl group, methoxypropyl group, methoxybutyl group, ethoxyethyl group or propyloxypropyl group; and
(c) an arylalkyl group which may have a substituent, e.g., benzyl group, phenethyl group, phenylpropyl group or naphthylmethyl group.

The substituent for the linear or branched alkyl group (a) and the alkoxyalkyl group (b) includes, for instance, a halogen atom such as fluorine atom, chlorine atom, bromine atom or iodine atom. The substituent for the arylalkyl group (c) includes, for instance, a linear or branched lower alkyl group, e.g., methyl group, ethyl group, propyl group, isopropyl group, n-butyl group, sec-butyl group, t-butyl group, n-hexyl group, 2-hexyl group or 3-hexyl group; a linear or branched lower alkoxy group, e.g., methoxy group, ethoxy group, propyloxy group, isopropyloxy group, n-butoxy group, sec-butoxy group, t-butoxy group, n-hexyloxy group, 2-hexyloxy group or 3-hexyloxy group; a halogen atom, e.g., fluorine atom, chlorine atom, bromine atom or iodine atom; and the like.

Preferable examples of the ester residue of the ester compound (B') are, for instance, isopropyl group, n-butyl group, sec-butyl group, t-butyl group, n-pentyl group, n-hexyl group, n-octyl group, n-nonyl group, n-decyl group, benzyl group and phenethyl group, if the ester residue of the trans-3-substituted glycidic acid ester (I) is methyl group or ethyl group.

Further, the absolute configuration of the ester compound (B') may be either one of (2R,3S) and (2S,3R).

If the (2R,3S)-ester compound (B') is dissolved in the solution, the (2S, 3R)-isomer (A) can be crystallized to give crystals of high purity until the concentration of the (2S, 3R)-isomer (A) in the mother liquor becomes very low as compared with conventional processes. On the other hand, if the (2S,3R)-ester compound (B') is dissolved in the solution, the (2R,3S)-isomer (A) can be crystallized to give crystals of high purity until the concentration of the (2R, 3S)-isomer (A) in the mother liquor becomes very low as compared with conventional processes. Therefore, in either case, the desired product can be obtained in an extremely higher yield as compared with conventional processes.

Any solvent which can be used in recrystallization of trans-3-substituted glycidic acid esters (I) may also be employed as the crystallization solvent of the present invention. Examples of such crystallization solvents are, for instance, an alcohol solvent such as methanol, ethanol, n-propanol, isopropanol or n-butanol; an ether solvent such as diethyl ether, t-butyl methyl ether, diisopropyl ether, tetrahydrofuran or dioxane; an aromatic hydrocarbon solvent which may be substituted by a halogen atom, such as benzene, toluene, xylene, chlorobenzene or dichlorobenzene; an aliphatic hydrocarbon solvent which may be substituted by a halogen atom, such as hexane, cyclohexane, n-heptane, n-octane, dichloromethane, chloroform, 1,2-dichloroethane or carbon tetrachloride; an ester solvent such as methyl acetate or ethyl acetate; and the like. The solvents may be used alone or in an admixture thereof.

A suitable solvent may be selected depending on the ester residues of trans-3-substituted glycidic acid ester (I) and the ester compound (B') and the substituent on the phenyl group of the ester (I). It is preferable to use solvents in which the solubility of the optical isomer (A) of the trans-3-substituted glycidic acid ester (I) greatly varies depending on the temperature and the solubility of the ester compound (B') is far larger than that of the optical isomer (A). For example, when trans-3-(4-methoxyphenyl)glycidic acid methyl ester is used as the ester (I) and n-butyl ester thereof is used as the ester compound (B'), methanol, ethanol, xylene and the like are preferable as the solvent for dissolving these compounds.

The suitable amount of the solvent can be determined within the range that the optical isomers (A) and (B) and the ester compound (B') can be dissolved once and the isomer (A) can be crystallized by lowering the temperature of the solution. Thus, a proper range of the amount of solvent can be experimentally found according to the kind of optical isomers (A) and (B) and the ester compound (B'), proportion thereof, crystallization temperature and so on. In general, when solvents in which the solubility of the optical isomers (A) and (B) are large and the solubility is largely changed according to the temperature change is used, it may be possible to decrease the amount of the solvent.

For example, in case that the following mixture of trans-3-(4-methoxyphenyl)glycidic acid esters is dissolved in 100 ml of xylene and the resulting solution is cooled to −10° C., only (2R, 3S) methyl ester can be efficiently crystallized from the solution even in the range wherein the concentration of (2R, 3S) methyl ester in the solution is smaller than that of (2S, 3R) methyl ester.

| Mixture of the glycidic acid esters dissolved in 100 ml of xylene | |
|---|---|
| (2R,3S) methyl ester | 49 g |
| (2S,3R) methyl ester | 14 g |
| (2S,3R) n-butyl ester | 39 g |
| Composition of the glycidic acid esters remaining in the solution after crystallization of (2R,3S) methyl ester | |
| (2R,3S) methyl ester | 9 g |
| (2S,3R) methyl ester | no change |
| (2S,3R) n-butyl ester | no change |

The concentration of the optical isomer (A) in the solution prior to the crystallization may vary depending on the kinds of the isomer (A) and solvent, the temperature of the crystallization and the like, but it is usually from 0.5 to 4 moles/liter.

In a solution in the process of the present invention, the ratio of the optical isomer (A)/the optical isomer (B) is required to be within a range in which the optical isomer (A) is more easily crystallized than the optical isomer (B), the crystallization of which is inhibited by the ester compound (B').

Even under the (A)/(B) ratio wherein the optical isomer (B) would precipitate if the ester compound (B') were not present, the optical isomer (A) can be obtained as crystals by the process of the present invention.

Of course, the solution which contains the optical isomer (A) in an amount larger than the optical isomer (B) can be used and is preferred in the process of the present invention, since such an additional large amount of the optical isomer (A) can also be obtained as the crystals in addition to the crystals of the optical isomer (A) obtained by the inhibition of crystallization of isomer (B) due to the presence of ester compound (B'). Thus, it is possible to start the process of the present invention from a solution containing a larger amount of the isomer (A) than the isomer (B).

Moreover, the inhibitory effect of the ester compound (B') on crystallization of the optical isomer (B) increases according to the increase in the ratio of the ester compound (B')/the optical isomer (B), and the increased amount of the optical isomer (A) can be obtained. Thus, the higher the ratio of the ester compound (B')/the isomer (B) is, the more preferable the process of the present invention is.

The ratios of these compounds in the initial solution for the crystallization of the present invention vary depending on the kinds of the ester residues of the ester compound (B') and the solvent used in the crystallization. In general, the molar ratio of the optical isomer (A)/the optical isomer (B) is from about 4/6 to about 10/1, and the molar ratio of the ester compound (B')/the optical isomer (B) is from about 5/3 to about 10/1. Preferably, the molar ratio of the isomer (A)/isomer (B) is from about 1/1 to about 4/1, and the molar ratio of the ester compound (B')/isomer (B) is from about 2/1 to about 7.8/1.

In the process of the present invention, the crystallization can also be carried out from a solution containing other components than the isomers (A) and (B) and the ester compound (B'). For instance, in addition to these three components, the solution may contain an optical isomer (ester compound (A')) different from the optical isomer (A) only in the ester residue. In case that the ester compound (A') is contained in the solution, the molar ratio of the ester compound (A')/the isomer (A) is preferably at most 9/35 of the molar ratio of the ester compound (B') /the isomer (B), so that the inhibitory effect of the ester compound (A') on the crystallization of isomer (A) can be minimized and the isomer (A) can be obtained in a large amount and in high purity.

That is to say, the ester compound (A') may be present in the solution for the crystallization of the present invention so long as the optical isomer (A) is only crystallized due to the inhibitory effect of the ester compound (B') on the crystallization of the optical isomer (B) though the crystallization of the optical isomer (A) may be inhibited by the presence of the ester compound (A').

When the inhibitory effect of the ester compound (B') present in the solution on the crystallization of the isomer (B) is larger than that of the ester compound (A') on the crystallization of the isomer (A), the isomer (A) can be easily crystallized than the isomer (B), and the isomer (A) can be obtained by the process of the present invention.

In the process of the present invention, it is required that at least three isomers, namely the optical isomers (A) and (B) and the ester compound (B'), are present in the solution. In this respect, the process of the present invention is clearly different from a process A for preferential crystallization from a solution containing only the isomers (A) and (B). Also, the process of the present invention takes advantage of the inhibitory effect of the ester compound (B') on the crystallization of the isomer (B) and the isolation of the desired isomer (A) can be achieved by one crystallization-isolation procedure. In these respects, the process of the present invention is also different from the preferential crystallization process in which it is necessary to repeat the following steps (i) and (ii):

(i) seeding crystals of the optical isomer (A) to a solution containing only the isomers (A) and (B) to crystallize and isolate the optical isomer (A) and
(ii) seeding crystals of the optical isomer (B) to the solution resulting in the step (i) to crystallize and isolate the optical isomer (B).

Furthermore, the process of the present invention differs from the preferential crystallization, wherein the crystallization of an optical isomer must be carried out using a solution containing a larger amount of one optical isomer and a smaller amount of the other optical isomer. In contrast to this, according to the process of the present invention, the crystallization of an optical isomer (A) is possible in a wide range from the optical isomer (A) >> the optical isomer (B) in the solution to the optical isomer (A) < the optical isomer (B) therein.

Concomitantly, the process of the present invention includes the embodiment wherein the crystallization is carried out from a solution in which the crystals of the optical isomer (A) are also included. However, the crystallization of the optical isomer (A) from a solution not including at least one of the optical isomer (B) and the ester compound (B') is excluded from the present invention because no inhibition of the crystallization of the optical isomer (B) is possible.

The crystallization according to the process of the present invention must be carried out at a temperature at which the optical isomer (A) of trans-3-substituted glycidic acid ester (I) is crystallized, but the optical isomer (B) and the ester compound (B') do not precipitate.

The temperature at which the crystallization of the optical isomer (B) begins only after the solution is allowed to stand for some time is included within the temperature range of the present invention. Such crystallization temperature varies depending on the kind of trans-3-substituted glycidic acid ester (I), the kind of solvent and the composition of the solution to be subjected to crystallization. Considering the stability of the oxirane ring of trans-3-substituted glycidic acid ester (I), it is not desirable to prepare the crystallization solution by dissolving the optical isomers (A) and (B) and the ester compound (B') at a higher temperature. It is preferable that the dissolution is carried out at a temperature of not higher than 70° C., and the crystallization is carried out at a temperature not higher than room temperature.

Also, in general, when the amount of the solvent is large, the crystallization of the isomer (A) does not proceed unless the solution is cooled to a low temperature, while when the amount of the solvent is small, the crystallization proceeds even at a relatively high temperature. Therefore, when the process of the present invention is carried out on an industrial scale, it is preferable from the viewpoints of the amount of the solvent, installation and energy that the amount of the solvent is decreased and the crystallization is carried out from a concentrated solution at around room temperature.

On the other hand, when the crystallization is carried out from a concentrated solution, the product usually tends to contain an increased amount of impurities. Therefore, from the viewpoint of purity, it is preferable to use a large amount of a solvent and to carry out the crystallization at a low temperature.

For such reasons, in order to efficiently carry out the crystallization of the optical isomer (A), an optimum temperature range should be experimentally determined depending on the kind of trans-3-substituted glycidic acid ester (I), the ester residue of the ester compound (B'), the kind of the solvent used and the composition of the solution to be subjected to crystallization.

For instance, when the optical isomers (A) and (B) is methyl esters and the ester compound (B') is a n-butyl ester and the crystallization is carried out from methanol, it is preferable to carry out the crystallization at a temperature of 30° to +15° C. A similar temperature range may be applied for other cases.

In the process of the present invention, since the crystallization of the optical isomer (B) is inhibited by the ester compound (B'), the optical isomer (A) free from any contamination of the optical isomer (B) can be obtained without any very strict temperature control, which is necessary for the preferential crystallization, taking advantage of the difference in precipitation velocity between the optical isomers having the same solubility. Therefore, the allowable temperature range of the present invention is wider than the preferential crystallization process.

According to the process of the present invention, the crystallization of the optical isomer (B) is inhibited by the ester compound (B'). When precipitation of the optical isomer (B) occurs, the optical isomer (B) precipitates together with the ester compound (B') in an amorphous-like form. The crystallization of the optical isomer (A) is visually distinguished from such precipitation.

Concomitantly, the crystallization of the optical isomer (A) according to the present invention can be carried out from a solution containing the optical isomer (A) and (B) and the ester compound (B') up to the extent that the optical isomer (B) would precipitate if the ester compound (B') were not present. Since whether such extent is reached or not depends on the solubility of the optical isomers (A) and (B) and the ester compound (B'), even if the extent is not reached at a temperature, such extent may be reached at another temperature, and vice versa.

In the following lines, the condition under which the optical isomer (A) is crystallized from a solution containing the optical isomers (A) and (B) and the ester compound (B'), but the optical isomer (B) does not precipitate by the presence of the ester compound (B') though the optical isomer (B) would precipitate in the absence of the ester compound (B'), is explained by the use of FIG. 1 illustrating the extent to be reached by the process of the present invention by the use of the parameters of temperature and time. In this connection, it is assumed that the initial concentration of the optical isomer (A) in the solution is larger than that of the optical isomer (B) and the amount of the ester compound (B') in the solution is sufficient for the inhibition of the crystallization of the optical isomer (B).

The solution (a) is a completely homogeneous solution. If the solution (a) is cooled, the isomer (A) begins to crystallize at the point (b). If the cooling of the solution is further continued, the isomer (A) in excess of the isomer (B) in the solution crystallizes to reach the point (c) at which the molar ratio of the isomer (A)/the isomer (B) is 1/1.

Theoretically, it is possible that only the isomer (A) is crystallized during the cooling of the solution (a), i.e., from the point (b) to the point (c). However, in a process disclosed in Japanese Patent Publication Kokai No. 8-259552, the isomer (A) is crystallized only to the extent that the molar ratio of the isomer (A)/the isomer (B) in the mother liquor after the crystallization is about 1.3/1. This is because according to knowledge of general crystallization technique, if the solution (a) is cooled from the point (b) toward the point (c), the ratio of the optical isomer (B)/the optical isomer (A) in the solution increases through the precipitation of the crystals of the optical isomer (A) and the solubility of the optical isomer (B) decreases. Therefore, the fluctuation of the solution (i.e., partial non-uniformity of temperature, concentration and so on of the solution) exerts an influence on the crystallization of the isomer (B).

The solution at the point (c) contains isomers (A) and (B) in equal amounts. Therefore, when the solution is cooled from the point (c), the optical isomers (A) and (B) were considered to crystallize in the form of the equimolar mixture thereof.

Nevertheless, in the present invention, since the ester compound (B') is present in the solution, crystallization of the isomer (B) is inhibited thereby. Thus, even if the solution is further cooled from the point (c), the isomer (A) is crystallized, but the isomer (B) is not crystallized, so the yield of the isomer (A) can be increased.

After passing through the point (c), if the solution is further cooled to a lower temperature, the solution finally reaches the point (d) at which the whole solution becomes cloudy and not only the isomer (A) is crystallized, but also an amorphous-like form of the isomer (B) and the ester compound (B') precipitates. Therefore, it is necessary to carry out the process of the present invention at a temperature higher than the point (d).

After passing through the point (c), if the solution is further cooled, for example, to reach the point (e) and the solution is maintained for some time at that temperature, the solution reaches the point (f) after an elapse of time t, where the whole solution becomes cloudy and the same phenomenon as appearing at the point (d). Namely, the isomer (B) which has been inhibited from precipitation by the ester compound (B') precipitates together with the ester compound (B') as an amorphous-like form. Therefore, the process of the present invention is required to finish the crystallization and isolation of the optical isomer (A) before time t at which the solution becomes cloudy.

As explained above, the extent of crystallization aimed by the process of the present invention is within the region "the extent to be reached by the process of the invention" shown in FIG. 1. This region varies depending on various factors, e.g., the kind and ratio of the isomers (A) and (B) and the ester compound (B'), and the kind and amount of the solvent. Thus, the suitable region can be determined in accordance with these factors. For instance, in the case that the amount of the isomer (A) in the solution (a) as shown in FIG. 1 is smaller than that of the isomer (B), the starting point of the crystallization of the isomer (A) is somewhere between the points (d) and (c) and it is possible to crystallize and isolate the isomer (A) in pure form up to the point (d).

The isolation of crystalline isomer (A) may be carried out in a usual manner such as decantation and filtration. If the crystallization is carried out in a large scale, a long time is required for the isolation, though the isolation in small scale can be accomplished in a short time. In case of the isolation on a laboratory scale, even immediate isolation is possible. If the isolation requires a long time as in the case of industrial production, it is preferable to interrupt the crystallization, for instance, at the point (e), so that the isolation can be completed without any contamination within the time length up to the point t.

According to the process of the present invention, if the crystallization is carried out, for instance, from a solution containing racemic trans-3-(4-methoxyphenyl)glycidic acid methyl ester and (2S, 3R)-3-(4-methoxyphenyl)glycidic acid n-butyl ester, the amount of which is sufficient to inhibit the precipitation of the (2S,3R)-isomer of the methyl ester, it is possible to crystallize (2R, 3S)-3-(4-.4-; methoxyphenyl)glycidic acid methyl ester until the concentration of (2S, 3R)-3-(4-methoxyphenyl)glycidic acid methyl ester in the mother liquor after the crystallization becomes at least twice as much as that of (2R, 3S)-3-(4-methoxyphenyl)glycidic acid methyl ester. Further, it is also possible to obtain the crystals of the (2R,3S)-isomer having optical purity of at least 99%.

Thus, according to the present invention, after carrying out the crystallization of the optical isomer (A) without any precipitation of the optical isomer (B) until the amount of the isomer (A) in the mother liquor is equal to that of the isomer (B), it is possible to continue the crystallization of the isomer (A) in high purity until the amount of the isomer (A) in the mother liquor becomes smaller than that of the isomer (B).

Japanese Patent Publication Kokai No. 8-259552 discloses that crystals of (2R,3S)-3-(4-methoxyphenyl)glycidic acid methyl ester having optical purity of at least 99% are obtained by asymmetrically transesterifying racemic trans-3-(4-methoxyphenyl)glycidic acid methyl ester in the presence of an esterase derived from Serratia marcescens to convert 7.8/8.8 (about 88.6%) of the (2S,3R)-isomer into the n-butyl ester, removing the enzyme, distilling away the solvent under reduced pressure, and then conducting crystallization from isopropanol.

However, the crystallization is interrupted at the stage that the amount of the desired (2R,3S)-3-(4-methoxyphenyl) glycidic acid methyl ester in the mother liquor after the crystallization is about 1.3 times as much as that of (2S, 3R)-3-(4-methoxyphenyl)glycidic acid methyl ester. This is because it was considered to be necessary to interrupt the crystallization so as to avoid the contamination by the crystallization of the undesired (2S, 3R)-isomer.

In contrast, according to the present invention, the crystallization can be carried out until the amount of the desired (2R, 3S)-3-(4-methoxyphenyl)glycidic acid methyl ester in the mother liquor after the crystallization becomes about half of the undesired (2S, 3R)-3-(4-methoxyphenyl)glycidic acid methyl ester.

The extent to which the isomer (A) is crystallized, namely the extent up to which the crystallization is continued, varies depending on the ratio of trans-3-substituted glycidic acid ester (I)/ester compound (B'), solvent for crystallization, crystallization temperature and the like. However, since the solution subjected to the crystallization becomes cloudy at a stage that an amorphous-like form of the isomer (B) and the ester compound (B') begins to precipitate, it is possible to recognize the end point of the crystallization of the isomer (A) by monitoring the appearance of cloudiness in the solution.

The purity of crystals may be generally affected by concentration of a solution to be subjected to crystallization (or the ratio of a solvent/the amount of the optical isomers), the ratio of optical isomer (A)/optical isomer (B), temperature, amount of crystals obtained and the like.

Generally speaking, the purity of the crystals of the optical isomer (A) tends to be high if the crystallization is carried out up to the extent that the isomers (A) and (B) are hard to be crystallized and the amount of the precipitated crystals of the optical isomer (A) is small. For example, if the concentration of the isomers (A) and (B) in the crystallization solution is low, the ratio of the isomer (A)/the isomers (A) and (B) is high, the crystallization temperature is high and the amount of crystals of the optical isomer (A) is small, the purity of the crystalline isomer (A) is high. In contrast to this, the yield of the crystals of the optical isomer usually tends to be low if the concentration is low.

However, according to the present invention, the precipitation of the optical isomer (B) is inhibited on account of the presence of the ester compound (B') and thus, it is possible to obtain optical isomer (A) having purity higher than 99% in a high yield.

The crystallization procedure is very simple since it comprises merely conducting the crystallization of the optical isomer (A) from a solution of the optical isomers (A) and (B) and the ester compound (B') up to the extent that the optical isomer (B) does not precipitates due to the presence of the ester compound (B') though the optical isomer (B) would precipitate in the absence of the ester compound (B'), thereby the crystallization is continued up to the range where the amount of the optical isomer (A) is smaller than that of the optical isomer (B) in the mother liquor of the crystallization.

In conventional crystallization, crystals of the optical isomer (A) are obtained by crystallizing from a solution (AB) containing the optical isomers (A) and (B) up to the extent that the amount of the isomer (A) in the mother liquor is larger than that of the isomer (B). In such crystallization, the solvent, temperature and the concentration were carefully selected respectively in order to obtain the optical isomer (A) in high purity without any crystallization of the optical isomer (B), but the yield of the optical isomer (A) was obliged to be sacrificed to some extent.

However, according to the process of the present invention, the optical isomer (A) can be crystallized without precipitation of the isomer (B) even up to the extent that both of the optical isomers (A) and (B) would be crystallized in the conventional crystallization wherein the ester compound (B') were absent in the crystallization solution.

The preparation of the solution (ABB') and the solution. (AA'BB') to be subjected to the crystallization is explained below.

The ester compound (A') may act to lower the yield of isomer (A) and, therefore, it is preferable that a solution to be subjected to the crystallization does not contain the ester compound (A'). Since the ester compound (A') is not a component to be positively added to the solution though such contamination may in some cases not be avoidable in preparing the solution, the solution (ABB') is more preferable than the solution (AA'BB').

The solution (ABB') can be prepared, for instance, by adding the ester compound (B') to a solution (AB) containing the optical isomers (A) and (B) or by transesterfying the optical isomer (B) in the solution (AB) to an ester compound (B') in the presence of an enzyme having a stereoselective transesterification ability by the use of an alcohol ($R^3$—OH in which $R^3$ is a linear or branched alkyl group which may be substituted, an alkoxyalkyl group which may be substituted or an arylalkyl group which may be substituted).

In case of the enzymatic transesterification, the solution (ABB') is obtained only when the stereoselectivity of an enzyme is 100%, and an enzyme having a stereoselectivity of less than 100% gives the solution (AA'BB'). Therefore, it is preferable to use an enzyme having a good stereoselectivity.

The solution (AB) is usually obtained by a chemical synthesis since the product thereof is an equimolar mixture of the optical isomers with the exception of asymmetric synthesis.

The ester compound (B') remains in a high concentration in a mother liquor from which the optical isomer (A) has been crystallized and isolated according to the present invention and can be taken out therefrom if necessary. The ester compound (B') can also be obtained by enzymatically and selectively hydrolyzing ester compound (A') in a mixture of ester compounds (Al) and (B').

In case of preparing the solution (ABB'), the ester compound (B') is usually added to a solution (AB) so that the resulting solution (ABB') satisfies the condition that the isomer (A) is crystallized, but the isomer (B) is not crystallized by the presence of the ester compound (B').

Solution (AB) to which ester compound (B') is added, is not limited to a solution of an equimolar mixture of the optical isomers (A) and (B), and may be a solution containing the isomers (A) and (B) in different amounts. For example, such solution (AB) may be prepared by an asymmetric synthesis as disclosed, for instance, in Japanese Patent Publication Kokai No. 61-268663, No. 2-17170 and No. 2-17169, WO 89/02428 and WO 89/10350.

The solution (AB) containing the isomers (A) and (B) in different amounts may also be a solution prepared by subjecting a racemic solution to an enzymatic and asymmetric hydrolysis disclosed in, for example, Japanese Patent Publication Kokai No. 2-109995 and No. 3-15398 and Japanese Patent Publication Kohyo No. 4-501360, or by subjecting a racemic solution to chemical optical resolution as disclosed for example in Japanese Patent Publication Kokai No. 61-145174 and No. 2-231480.

As mentioned above, the process of the present invention may be carried out in combination with known processes, e.g., asymmetric synthesis, chemical or enzymatic optical resolution and so on. In these cases, even if the asymmetric induction or the rate of optical resolution in the known processes is insufficient, the optical isomer (A) having a high purity can be recovered in a good yield by combining such insufficient process with the process of the present invention.

Also, the process of the present invention may be applied to a solution prepared by subjecting a solution (AB) to an enzymatic transesterification instead of adding ester compound (B') to the solution (AB). For example, the process of the present invention is applicable to a solution. (ABB') obtained in the process disclosed in Japanese Patent Publication Kokai No. 4-228095, No. 6-78790 and No. 8-259552 wherein (2R,3S)-3-(4-methoxyphenyl)glycidic acid methyl ester is obtained by subjecting racemic trans-3-(4-methoxyphenyl)glycidic acid methyl ester to enzymatic asymmetric transesterification with n-butanol to convert the (2S,3R)-isomer.

Various applications and modifications of the process of the present invention are possible. For example, both of the optical isomers (A) and (B) can be obtained in high purity by way of a recycling process which comprises:

(a) preparing a solution of one optical isomer (A) and the other optical isomer (B) of the ester compound (I), both of which are the optical isomers due to the asymmetric carbons at 2- and 3-positions, and an ester compound (B') which is different from the isomer (B) only in the ester residue $R^1$, (b) crystallizing the optical isomer (A) from the solution up to the extent that the optical isomer (A) is crystallized without the precipitation of the optical isomer (B) due to the presence of the ester compound (B') though the optical isomer (B) would precipitate if the ester compound (B') were not present, (c) isolating the crystals of the optical isomer (A), (d) chemically transesterfying the ester compound (B') included in the resulting mother liquor together with the remaining optical isomers (A) and (B) so as to convert the ester compound (B') into the optical isomer (B) followed by the crystallization and isolation of the isomer (B), (e) adding a racemic trans-3-substituted glycidic acid ester (I) and an ester compound (B') to the resulting mother liquor to provide a solution to be subjected to the crystallization of step (b), and (f) repeating the above-mentioned steps (b), (c), (d) and (e) in this order.

In the recycling process, the concentration of the isomer (B) in the reaction mixture of the chemical transesterification in the step (d) is higher than that of the isomer (A) and, therefore, only the isomer (B) can be obtained by conducting a conventional crystallization and isolation.

If an ester compound (A') is added to the reaction mixture of the chemical transesterification prior to crystallizing the isomer (B) in the step (d), the isomer (B) can be more efficiently crystallized by an inhibitory effect of the ester compound (A') on the crystallization of the isomer (A). In case that the ester compound (A') is added in the step (d), such ester compound (A') included in the resulting mother liquor is chemically transesterified to the isomer (A) in the step It is preferable that the amount of the ester compound (A') added in the step (d) corresponds to that of the ester compound (B') included in the solution in the step (a). The amount of the ester compound (A') varies depending on the ester residues of the isomers (A) and (B) and the ester compound (A') and the solvent used for the crystallization, but in general the amount of the ester compound (A') may be adjusted so that the molar ratio of ester compound (A')/ isomer (A) is from about 5/3 to about 10/1.

The chemical transesterification adopted in the recycling process is carried out by adding an organic amine and an alcohol corresponding to the ester residue of an optical isomer to be obtained to the mother liquor obtained in the step (c), and conducting the transesterification followed by distilling away the organic amine and the alcohol. The chemical transesterification of the ester compound (A') is carried out in the same manner.

The amount of the alcohol to be used in the chemical-transesterification may be preferably from 1 to 1,000 moles, especially 2 to 10 moles, per mole of an ester to be transesterified. Alcohols having a low boiling point, e.g., methanol or ethanol can be preferably used for the chemical transesterification in view of the recycling of the isomers (A) and (B).

Examples of the amine used in the chemical transesterification are, for instance, a monoalkylamine (e.g., methylamine, ethylamine, propylamine, butylamine); a dialkylamine (e.g., dimethylamine, diethylamine, dipropylamine, diisopropylamine); a trialkylamine (e.g., trimethylamine, triethylamine); a cyclic amine (e.g., morpholine); and an aromatic amine (e.g., pyridine). Use of a dialkylamine having a low boiling point, e.g., dimethylamine, dipropylamine or diisopropylamine is particularly preferred. The organic amine is preferably used in an amount of 0.01 to 1,000 moles, especially 0.1 to 10 moles, per mole of the ester to be transesterified.

When the above recycling process is conducted, both of the isomers (A) and (B) can be obtained in high purity in one cycle. Since the process can be practically carried out infinitely if the organic amine and alcohol can be sufficiently distilled away after the chemical transesterification, the isomers (A) and (B) having a high purity can be efficiently obtained only by recycling the process without conducting an asymmetric chemical reaction.

Moreover, the decrease in optical purity due to the contamination of the antipode on account of the fluctuation (partial nonuniformity in solution temperature, concentration and so on) of a crystallization solution can be suppressed and the amounts of the optical isomers obtained in one cycle is large. Therefore, the recycling process is industrially advantageous.

A process wherein a solution containing optical isomers (A) and (B) and ester compound (B') is prepared by a transesterification process and is then applied to the process of the present invention is explained below.

It is preferable to prepare a solution to be used for the crystallization of optical isomer (A) by enzymatically transesterifying the isomer (B) in a solution of optical isomers (A) and (B) into the ester compound (B'), since it is possible to obtain in a single reaction step a solution containing a larger amount of the isomer (A) and a smaller amount of the isomer (B) together with the ester compound (B') which inhibits crystallization of the isomer (B).

In the process of the present invention, it is preferable for the ratio of the isomer (A)/the isomer (B) in the reaction mixture resulting from the transesterification to be as large as possible. In other words, it is preferable for the ester compound (B') to be abundant in the reaction mixture. In this case, in order to decrease the amount of the isomer (B) therein, it is necessary, for example, to increase the amounts of the enzyme and the alcohol used for the transesterification and to conduct the reaction for a longer time. However, such procedures increase the cost and cause side reactions.

According to the process of the present invention, even if the degree of transesterification is low, the resulting solution may be successfully used for the optical resolution unlike conventional processes. This is because that the ester compound (B') inhibits precipitation of the isomer (B). The isomer (A) can be obtained in high purity in a high yield so long as the molar ratio of isomer (A)/isomer (B) is from 4/6 to 10/1 and the molar ratio of ester compound (B')/isomer (B) is from 5/3 to 10/1. It is particularly preferable that the molar ratio of isomer (A)/isomer (B) is from 3/1 to 4/1 and the molar ratio of ester compound (B')/isomer (B) is from 2/1 to 7.8/1.

The alcohols used for the transesterification are those which corresponds to the above-mentioned ester residue of the ester compound (B').

Any enzymes having an ability of stereoselectively transesterifying trans-3-substituted glycidic acid ester (I) with the alcohol may be used in the transesterification.

Such enzymes capable of selectively transesterifying the (2S, 3R)-isomer of the trans-3-substituted glycidic acid ester (I) include, for instance, esterases derived from microorganisms belonging to the genera Serratia, Candida, Mucor, Pseudomonas, Aspergillus, Alcaligenes, Absidia, Fusarium, Giberella, Neurospora, Trichoderma, Rhizopus, Achromobacter, Bacillus, Brevibacterium, Corynebacterium, Providencia, Saccharomycopsis, Nocardia and Arthrobacter, α-chymotrypsin, porcine heper esterase, porcine pancreas esterase, and the like.

Representative examples of the above-mentioned enzyme are, for instance, esterases derived from *Absidia corymbifera* IFO 4009 and IFO 4010, *Aspergillus ochraceus* IFO 4346, *Aspergillus terreus* IFO 6123, *Fusarium oxysporum* IFO 5942, *Fusarium oxysporum* ATCC 659, *Fusarium solani* IFO 5232, *Gibberella fujikuroi* IFO 5368, *Mucor angulimacrosporus* IAM 6149, *Mucor circinelloides* IFO 6746, *Mucor flavus* IAM 6143, *Mucor fragilis* IFO 6449, *Mucor genevensis* IAM 6091, *Mucor globosus* IFO 6745, *Mucor janssenii* IFO 5398, *Mucor javanicus* IFO 4569, IFO 4570, IFO 4572 and IFO 5382, *Mucor lamprosporus* IFO 6337, *Mucor petrinsularis* IFO 6751, *Mucor plumbeus* IAM 6117, *Mucor praini* IAM 6120, *Mucor pusillus* IAM 6122, *Mucor racemosus* IFO 4581, *Mucor ramannianus* IAM 6128, *Mucor recurvus* IAM 6129, *Mucor silvaticus* IFO 6753, *Mucor spinescens* IAM 6071, *Mucor subtilissimus* IFO 6338, *Neurospora crassa* IFO 6068, *Rhizopus arrhizus* IFO 5780, *Rhizopus delemar* ATCC 34612, *Rhizopus japonicus* IFO 4758, *Trichoderma viride* IFO 4847, *Achromobacter* cycloclastes IAM 1013, Bacillus sphaericus IFO 3525, Brevibacterium ketoglutamicum ATCC 15588, Corynebacterium alkanolyticum ATCC 21511, Corynebacterium hydrocarboclastum ATCC 15592, Corynebacterium primorioxydans ATCC 31015, Providencia alcalifaciens JCM 1673, Pseudomonas mutabilis ATCC 31014, Pseudomonas putida ATCC 17426,ATCC 17453and ATCC 33015, Serratia liquefaciens ATCC 27592, Serratia marcescens ATCC 13880, ATCC 14764,ATCC 19180,ATCC 21074,ATCC 27117and ATCC$_{21212,}$ Serratia marcescens Sr4l FERM BP-487, Candida parapsilosis IFO 0585, Saccharomycopsis lipolytica IFO 0717, IFO 0746, IFO 1195, IFO 1209 and IFO 1548, Nocardia asteroides IFO 3384, IFO 3424 and IFO 3423, Nocardia gardneri ATCC 9604, Arthrobacter ureafaciens nov. var., Arthrobacter globiformis and Candida cylindracea.

Commercially available enzymes are also usable, e.g., alkaline lipase (from Achromobacter, Wako Pure Chemical Industries, Ltd.), Lipase B (from Pseudomonas fragi 22-39B, Wako Pure Chemical Industries, Ltd.), Lipase M AMANO" 10 (from Mucor javanicum, Amano Seiyaku Kabushiki Kaisha), Lipase type XI (from Rhizopus arrhizus, Sigma Chemical Co., Ltd.), Talipase (from Rhizopus delemar, Tanabe Seiyaku Co., Ltd.), Lipase NK-116 (from Rhizopus japonicus, Nagase Sangyo Kabushiki Kaisha), Lipase N (from Rhizopus niveus, Amano Seiyaku Kabushiki Kaisha), Lipase SP 435 & 535 (from Candida antarctica, Novo), Alcalase (from Bacillus licheniformis, Novo), Lipase type VII (from Candida cylindracea, Sigma Chemical Co., Ltd.), lipase (from porcine pancreas, Wako Pure Chemical Industries, Ltd.), esterase (from porcine heper, Sigma Chemical Co., Ltd.), cholesterol esterase (from Candida rugosa, Nagase Sangyo Kabushiki Kaisha), Lipase OF (from Candida cylindracea, Meito Sangyo Kabushiki Kaisha), Lipase QL (from Alcaligenes sp., Meito Sangyo Kabushiki Kaisha), Lipase AL (from Achromobacter sp., Meito Sangyo Kabushiki Kaisha), and Lipase PL (from Alcaligenes sp., Meito Sangyo Kabushiki Kaisha).

Among these enzymes, preferred are esterases derived from microorganisms belonging to the genera Serratia, Candida, Alcaligenes and Achromobacter, particularly esterases derived from microorganisms such as Serratia marcescens and Candida cylindracea On the other hand, enzymes capable of selectively transesterifying the (2R, 3S)-isomer of the trans-3-substituted glycidic acid ester (I) include, for instance, esterases derived from microorganisms belonging to the genera Micrococcus, Agrobacterium, Microbacterium, Rhizobium, Citrobacter, Debaryomyces, Hanseniaspora, Hansenula, Pichia, Rhodosporidium, Schizosaccharomyces, Sporobolomyces, Kloeckera, Torulaspora and Streptomyces and the like.

Representative examples of such microbial enzymes capable of selectively transesterifying the (2R,3S)-isomer are, for instance, esterases derived from Micrococcus ureae IAM 1010 (FERM BP-2996), Agrobacterium radiobacter IAM 1526 and IFO 13259, Microbacterium sp. ATCC 21376, Rhizobium melioti IFO 13336, Citrobacter freundii ATCC 8090, Debaryomyces hansenii var. fabryi IFO 0015, Devaryomyces nepalensis IFO 0039, Hanseniaspora valbyens IFO 0115, Hansenula polymorpha IFO 1024, Hansenula saturnus HUT 7087, Pichia farinosa IFO 0607, Pichia pastoris IFO 0948, IFO 1013 and IAM 12267, Pichia wickerhamii IFO 1278, Rhodosporidium toruloides IFO 0559, Schizosaccharomyces pombe IFO 0358, Sporobolomyces gracillis IFO 1033, Kloeckera corticis IFO 0633, Torulaspora delbrueckii IFO 0422, Streptomyces griseus subsp. griseus IFO 3430 and IFO 3355, and Streptomyces lavendulae subsp. lavendulae IFO 3361, IFO 3415 and IFO 3146.

The enzymes used in the present invention may be commercially available enzymes or enzymes obtained from a culture broth of microorganism cells. Also, the enzymes may be those obtained from wild strains or mutants, or those obtained from microorganisms obtained by a biotechnological technique such as gene recombination or cell fusion.

The microbial enzymes as mentioned above can be obtained by culturing a microorganism in a conventional manner, for instance, in a medium containing usual carbon sources, nitrogen sources and inorganic salts at room temperature or an elevated temperature under aerobic conditions at pH of 5 to 8, removing the cells from the culture broth in a usual manner such as centrifugation or filtration, and optionally further removing an impurity with a resin adsorbent. The culture broth of a microorganism may be directly used as the enzyme.

The thus obtained solution may be directly used as the enzyme or may be lyophilized. Also, the enzymes may be immobilized by a known method such as a polyacrylamide method, a sulfur-containing polysaccharide gel method (e.g., carrageenin gel method), an agar gel method, a photo-crosslikable resin method, a polyethylene glycol method, a Celite method or a membrane adsorption method. The immobilized enzymes may be filled in a column and used in the transesterification.

Meanwhile, enzymes with a high E-value have a high stereoselectivity. With such enzymes, optical isomer (A) is transesterified into ester compound (A') in a less amount, while the optical isomer (B) is transesterified into ester compound (B') in a larger amount. Since the amount of the ester compound (A') which inhibits precipitation of the desired isomer (A) must be decreased so as to increase the amount of isomer (A) crystallized while the precipitation of isomer (B) is inhibited by the ester compound (B'), enzymes having a high E-value are preferred among the enzymes as mentioned above.

The E-value is one of popular indications for representing the stereoselectivity of enzymes, and is an enzyme reaction velocity ratio with respect to respective stereoisomers per unit concentration (e.g., ratio of velocity of transesterification of the (2R, 3S)-isomer/that of (2S, 3R)-isomer).

In general, in case that the reaction has proceeded to a great degree, the E-value is strongly influenced by inactivation of enzyme, side reaction, measurement error and the like. Thus, the E-value as used herein is a value measured when the conversion rate is 10% (at the time when 10% of trans-dl-form has been transesterified) at which stage side reaction, reverse reaction and measurement error are slight.

The E-value is represented by the following equation, and is a value unique to each of enzymes.

$$E = \frac{\ln[(1-c)(1-ee(\text{optical isomer A}))]}{\ln[(1-c)(1+ee(\text{optical isomer A}))]}$$

wherein $$c = \frac{\text{amount of ester } A' + \text{amount of ester } B'}{\text{amount of isomer } A + \text{amount of isomer } B + \text{amount of ester } A' + \text{amount of ester } B'}$$

$$ee(\text{optical isomer } A) = \frac{\text{amount of isomer } A - \text{amount of isomer } B}{\text{amount of isomer } A + \text{amount of isomer } B}$$

Thus, if the E-value and the transesterification conversion rate are determined, the ratio of optical isomers after the transesterification can be determined regardless of the kind of enzyme, and it is possible to expect the optical purity and yield obtained therefrom.

The E-value preferable for the preparation of the solution to be subjected to the crystallization according to the present invention is at least 20, especially at least 50. Enzymes having a preferable E-value as mentioned above can be suitably selected experimentally.

The amount of the enzyme varies depending on the kind of enzyme used, form of use and the like. But, it is desirable to use an enzyme at an amount having an olive oil hydrolysis activity of $1\times10$ to $1\times10^5$U, especially $1\times10^2$ to $1\times10^4$U, per g of isomer (B).

The olive oil hydrolysis activity is estimated by measuring the amount of the fatty acid generated by the cleavage of the ester bond in olive oil by esterase according to the fat digesting power test reported in Iyakuhin Kenkyu, vol. 11, No. 3, 505-506(1980).

The transesterification reaction can be carried out in an appropriate solvent or in the absence of a solvent. Examples of the solvent are an aromatic organic solvent such as benzene, toluene or xylene; a halogenated aromatic organic solvent such as chlorobenzene or dichlorobenzene; an aliphatic organic solvent such as hexane, heptane or cyclohexane; a halogenated aliphatic organic solvent such as dichloromethane, chloroform, carbon tetrachloride or trichloroethane; a ketone solvent such as acetone, methyl ethyl ketone or methyl isobutyl ketone; an ether solvent such as dimethyl ether, diethyl ether, diisopropyl ether, tert-butyl methyl ether, tetrahydrofuran or 1,4-dioxane; an ester solvent such as ethyl acetate or butyl acetate; and the like.

In particular, toluene, xylene, hexane, carbon tetrachloride, tert-butyl methyl ether and diisopropyl ether are preferred, since deactivation of enzymes is small and the reaction proceeds in high velocity.

The concentration of the substrates, i.e., isomers (A) and (B), is preferably from about 0.02 to about 3 moles/liter, especially about 0.02 to about 2 moles/liter, since the reaction velocity is high and the installations for the transesterification reaction can be miniaturized. The amount of the alcohol for transesterification is preferably from 0.6 to 10 moles, especially 0.8 to 5 moles, per mole of the isomer (B), so that the enzyme can be prevented from deactivating and the reaction velocity can be enhanced.

Contamination of the reaction system with water causes hydrolysis at the same time of transesterification, thus resulting in decrease of yield when the obtained solution is applied to the process of the present invention. Therefore, it is preferable to carry out the reaction with avoiding as much as possible the presence of extra water exceeding that required for an enzyme to exhibit the transesterification activity. Further, the hydrolysis product is not soluble in some solvents and this leads to decrease purity of the desired product due to the contamination of such by-product.

The transesterification reaction is carried out at room temperature or an elevated temperature, preferably at a temperature of 10 to 50° C., especially 20 to 40° C.

The conversion rate in the transesterification reaction can be suitably selected in accordance with stereoselectivity of enzyme, yield of optical isomer (A) and the like. Such conversion rate can be freely adjusted by changing enzyme activity, reaction temperature, reaction time and the like in accordance with the substrate, trans-3-substituted glycidic acid ester (I), and the ester residue of ester compound (B').

In order to obtain optical isomer (A) of high purity in a high yield by a conventional process, it is generally required to raise the conversion rate in transesterification and to use an enzyme having very high selectivity.

However, in order to raise the conversion rate, at a stage that the reaction has proceeded to a great degree, the isomer (B) which remains in a small amount in the reaction mixture must be further transesterified. Therefore, it is industrially impossible to raise the conversion rate to a high level considering the facts that a large amount of expensive enzyme is necessary, the enzyme is easily deactivated during the long time reaction, unstable trans-3-substituted glycidic acid ester (I) is apt to be decomposed during the long reaction and some enzymatic transesterification of isomer (A) is inevitable due to the insufficient selectivity of enzyme.

For example, Japanese Patent Publication Kokai No. 8-259552 discloses that asymmetric transesterification of racemic trans-3-(4-methoxyphenyl)glycidic acid methyl ester using esterase derived from Serratia marcescens is conducted to convert (2S, 3R)-isomer of the racemic methyl ester into (2S, 3R)-n-butyl ester until the molar ratio of (2S,3R)-butyl ester/(2S,3R)-methyl ester becomes 7.8/1 [(2S, 3R)-methyl ester 10.8 g and (2S, 3R) n-butyl ester 101.85 g].

However, this transesterification is carried out in such a manner that the reaction is firstly conducted for 24 hours using esterase of $5\times10^5$U per mole of the substrate, and after distilling away a solvent under reduced pressure until the volume of the reaction mixture becomes ⅓, esterase of $5\times10^5$U is added and the reaction is further conducted for 16 hours. Such a procedure is substantially inapplicable to industrial production, since the reaction time is too long, the procedure is too complicated and the amount of expensive enzyme is too large.

In contrast, according to the present invention, optical isomer (A) of a high purity can be obtained in a high yield even if the conversion rate in transesterification is not raised to a high level.

For example, (2R, 3S)-3-(4-methoxyphenyl)glycidic acid methyl ester having purity of 99% or more can be obtained in a yield of at least 80% from the reaction mixture obtained by the transesterification of racemic trans-3-(4-methoxyphenyl)glycidic acid methyl ester using esterase derived from *Serratia marcescens* Sr41 FERM BP-487 ($1\times10^5$U, 24 hours), wherein only 70% of the (2S, 3R)-isomer is converted into the n-butyl ester (ester compound B'/optical isomer B=7/3).

The present invention encompasses an embodiment wherein crystals of the substrate remain in the reaction mixture during the transesterification reaction for the reason that the solubility of the substrate is low in some solvent.

In this case, after the transesterification reaction wherein the undesired isomer is converted into a soluble ester compound, the desired product may be obtained from the reaction mixture by:

filtering the mixture of the enzyme and the desired isomer in crystals and removing the enzyme contaminated in the desired isomer, while the filtrate is cooled and the resulting crystals are obtained by filtration, or directly cooling the reaction mixture, filtering the mixture of the enzyme and the desired isomer in crystals and removing the enzyme therefrom.

The present invention also encompasses an embodiment wherein no crystals precipitate during the transesterification when the reaction is conducted in a normal procedure, but the crystals precipitate by positively distilling away the solvent in the course of the reaction. The separation of the crystals precipitated by distillation of the solvent can be conducted in the same manner as above. In case of distilling away a large portion of the solvent and adding a different solvent to the reaction mixture, the separation of the crystals can also be conducted in the same manner mentioned above.

In that case, an alcohol resulting from the transesterification can also be removed to the outside of the reaction system at the same time of the distillation of the solvent and, therefore, the subsequent transesterification comes to easily proceed.

As mentioned above, the process of the present invention is advantageous in that the optical isomer (A) of trans-3-substituted glycidic acid ester (I) is preferably manufactured in industrial scale. This is because the isomer (A) can be obtained in high purity and in a high yield by coupling the crystallization and the transesterification, which by itself was considered to be industrially inapplicable, even if the transesterification of the racemate is stopped at a stage wherein the conversion rate is low.

The above explanation has been made with respect to a process wherein optical isomer (A) is isolated by crystallizing the isomer (A) up to the extent that the isomer (B) is not crystallized due to the presence of the ester compound (B') although optical isomer (B) would precipitate if ester compound (B') were not present.

However, according to the process of the present invention, it is also possible to obtain the crystals of the optical isomer (A) in an amount larger as compared with the conventional methods wherein the isomer (A) is crystallized from a solution (AB) under the condition that the isomer (A) is crystallized, but the isomer (B) is not. This is because the ester compound (B') in the solution (AA'BB') or (ABB') inhibits the precipitation of the optical isomer (B) therefrom.

Moreover, the optical isomer (A) can be obtained in high purity and in a high yield in comparison of the conventional methods even from the solution (ABB') or the solution (AA'BB') obtained by the transesterification at low conversion rate.

For example, the isomer (A) of trans-3-substituted glycidic acid ester (I) is obtained in the form of crystals having optical purity of more than 99% in a yield of more than 75% (in particular more than 80%) by transesterifying the mixture of the isomers (A) and (B) with an alcohol corresponding to the ester compound (B') using an enzyme having an ability of stereoselectively transesterifying the isomer (B) to the ester compound (B') (especially having the E-value of more than 20, e.g., esterase derived from *Serratia marcescens* Sr41 FERM BP-487) until the molar ratio of ester compound (B')/isomer (B) becomes 13/7 to 7.8/1 (especially 2/1 to 8/2) and crystallizing the isomer (A) from the resulting reaction solution (the solvent of which may be exchanged).

Concomitantly, the above-mentioned reaction solution, the solvent of which is exchanged, includes, for instance, those obtained by partially or totally exchanging the solvent of the reaction solution so as to remove the resulting alcohol during the transesterification or by partially or totally exchanging the solvent after the transesterification so that the transesterification is carried out in a suitable solvent and the crystallization is accomplished in a proper solvent for that purpose.

The solution obtained by the transesterification may also be a solution obtained by removing the enzyme from the reaction mixture resulting from the transesterification in a conventional manner such as filtration or decantation.

From (2R,3S)-isomer of the trans-3-substituted glycidic acid ester, which is obtained above as the optical isomer (A), (2S, 3S)-1,5-benzothiazepine derivatives or pharmaceutically acceptable salts can be prepared by various processes, for example, by those disclosed in Japanese Patent Publication Kokoku No. 46-16749, Kokoku No. 63-13994, Kokai No. 5-201865, Kokai No. 2-289558 and Kokoku No. 2-28594, Chem. Pharm. Bull., 18(10), 2028-2037(1970), and Japanese Patent Publication Kokai No. 2-17168, No. 4-234866, No. 5-222016, No. 4-221376, No. 5-202013, No. 2-17170, No. 2-286672, No. 6-279398, No. 58-99471, No. 8-269026, No. 61-118377, No. 6-228117 and No.2-78673, European Patent Publication No. 796853 and Dutch Patent Publication No. 1006293.

Namely, (2S,3S)-1,5-benzothiazepine derivatives or pharmaceutically acceptable salts can be prepared by:

reacting the (2R,3S)-isomer with an aminothiophenol derivative of the formula (IV):

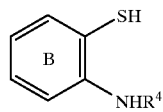

(IV)

wherein the ring B is as defined above, and R4 is hydrogen atom, 2-(dimethylamino)ethyl group or a group of the formula:

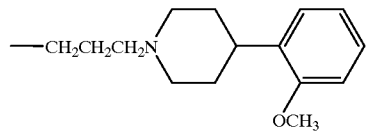

e.g., 2-aminothiophenol, 2-amino-5-chlorothiophenol, 2-amino-5-benzylthiophenol, 2-(dimethylaminoethylamino)-thiophenol or a compound of the formula:

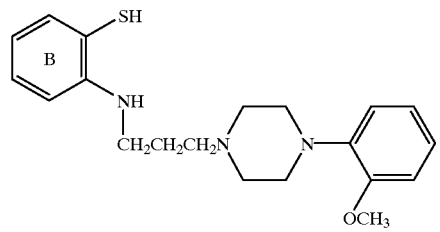

wherein the ring B is as defined above, or reacting the (2R, 3S)-isomer with a nitrothiophenol derivative of the formula (V):

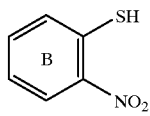

(V)

wherein the ring B is as defined above, e.g., 2-nitrothiophenol, 2-nitro-5-chlorothiophenol or 2-nitro-5-benzylthiophenol, followed by reduction of the nitro group, to give a (2S, 3S)-3-(2-aminophenylthio)-3-phenyl-2-hydroxypropionic acid ester of the formula (VI):

(VI)

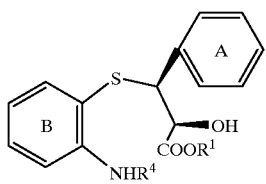

wherein the rings A and B, $R^1$ and $R^4$ are as defined above, subjecting the resulting compound (VI) to intramolecular ring closure directly or after conducting hydrolysis thereof, to give a (2S, 3S)-2-phenyl-3-hydroxy-1,5-benzothiazepine derivative of the formula (VII):

(VII)

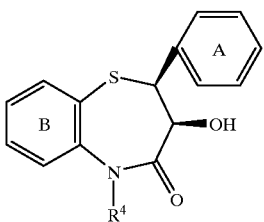

wherein the rings A and B and $R^4$ are as defined above, and subjecting the resulting compound (VII) to dimethylaminoethylation at nitrogen atom of the 5-position and acetylation of hydroxyl group substituted on the 3-position in arbitrary order to give a (2S, 3S)-1,5-benzothiazepine derivative of the formula (II):

(II)

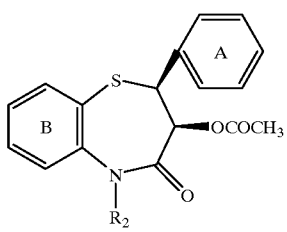

wherein the rings A and B and $R^2$ are as defined above, or a pharmaceutically acceptable salt thereof.

The total reaction scheme of the above-mentioned conversion is shown below.

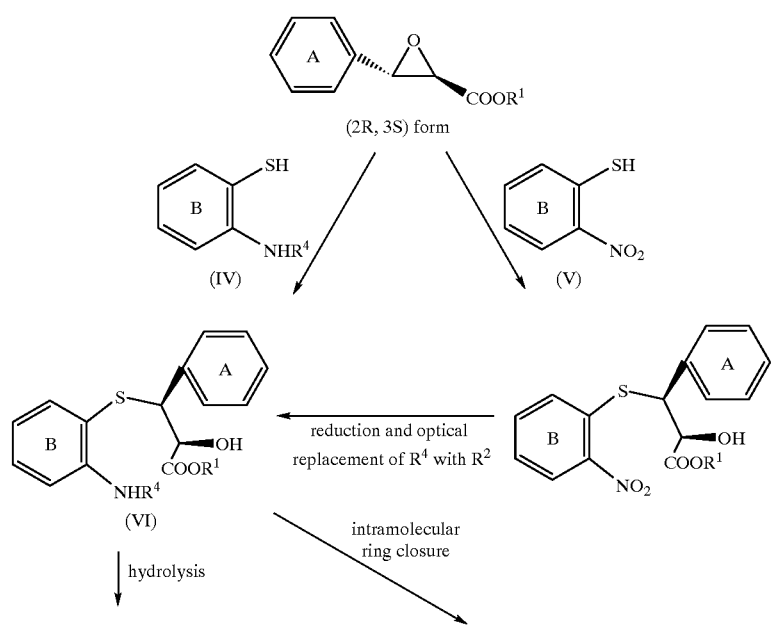

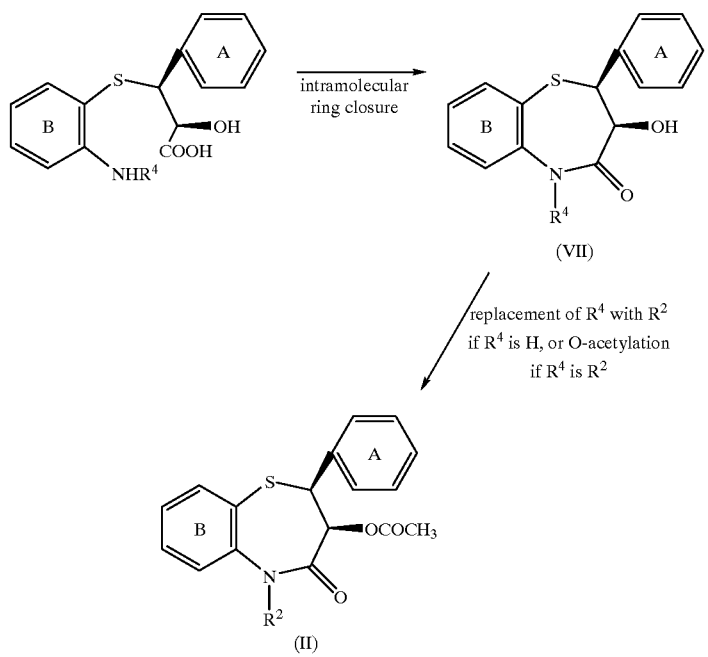

Examples of the (2S, 3S)-1,5-benzothiazepine derivatives (II) and the pharmaceutically acceptable salts thereof are, for instance, (2S, 3S)-2-(4-methoxyphenyl)-3-acetoxy-5-[2-(dimethylamino)ethyl]-2,3-dihydro-1,5-benzothiazepin-4 (5H)-one (diltiazem), (2S, 3S)-2-(4-methoxyphenyl)-3-acetoxy-5-[2-(dimethylamino)ethyl]-8-chloro-2,3-dihydro-1,5-benzothiazepin-4 (5H)-one, (2S, 3S)-3-acetoxy-5-[3-[4-(2-methoxyphenyl)-1-piperazinyl]propyl]-2,3-dihydro-2-(4-methoxyphenyl)-8-chloro-1,5-benzothiazepin-4(5H)-one, (2S, 3S)-3-acetoxy-8-benzyl-2,3-dihydro-5-[2-(dimethylamino)ethyl]-2-(4-methoxyphenyl)-1,5-benzothiazepin-4 (5H)-one, and pharmaceutically acceptable salts thereof.

Meanwhile, from (2S, 3R)-isomer of the trans-3-substituted glycidic acid ester, which is obtained above as the optical isomer (A), (2R,3R)-1,5-benzothiazepine derivatives or pharmaceutically acceptable salts can be prepared in a similar manner to the above according to the known processes.

Namely, (2R, 3R)-1,5-benzothiazepine derivatives or pharmaceutically acceptable salts can be prepared by:

reacting the (2S, 3R)-isomer with aminothiophenol derivative (IV), or reacting nitrothiophenol derivative (V) followed by reduction of the nitro group, in the same manner as the above-mentioned preparation of (2S,3S)-1,5-benzothiazepine derivatives (II) from the (2R, 3S)-isomer, to give a (2R, 3R)-3-(2-aminophenylthio)-3-phenyl-2-hydroxypropionic acid ester of the formula (VIII):

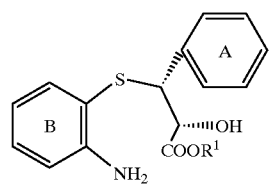

(VIII)

wherein ring A, ring B and $R^1$ are as defined above, subjecting the resulting compound (VIII) to intramolecular ring closure directly or after conducting the hydrolysis thereof, to give a (2R, 3R)-2-phenyl-3-hydroxy-1, 5-benzothiazepine derivative of the formula (IX):

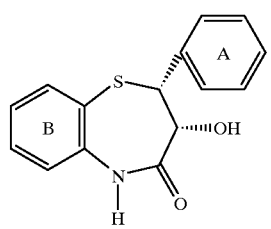

(IX)

wherein ring A and ring B are as defined above, and subjecting the resulting compound (IX) to dimethylaminoethylation at nitrogen atom of the 5-position and acetylation of hydroxyl group substituted on the 3-position in arbitrary order to give a (2R,3R)-1,5-benzothiazepine derivative of the formula (III):

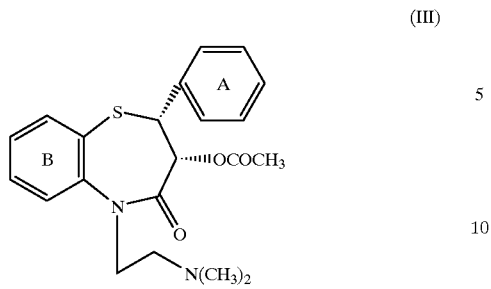
wherein ring A and ring B are as defined above, or a pharmaceutically acceptable salt thereof.
The total reaction scheme of the above-mentioned conversion is shown below.
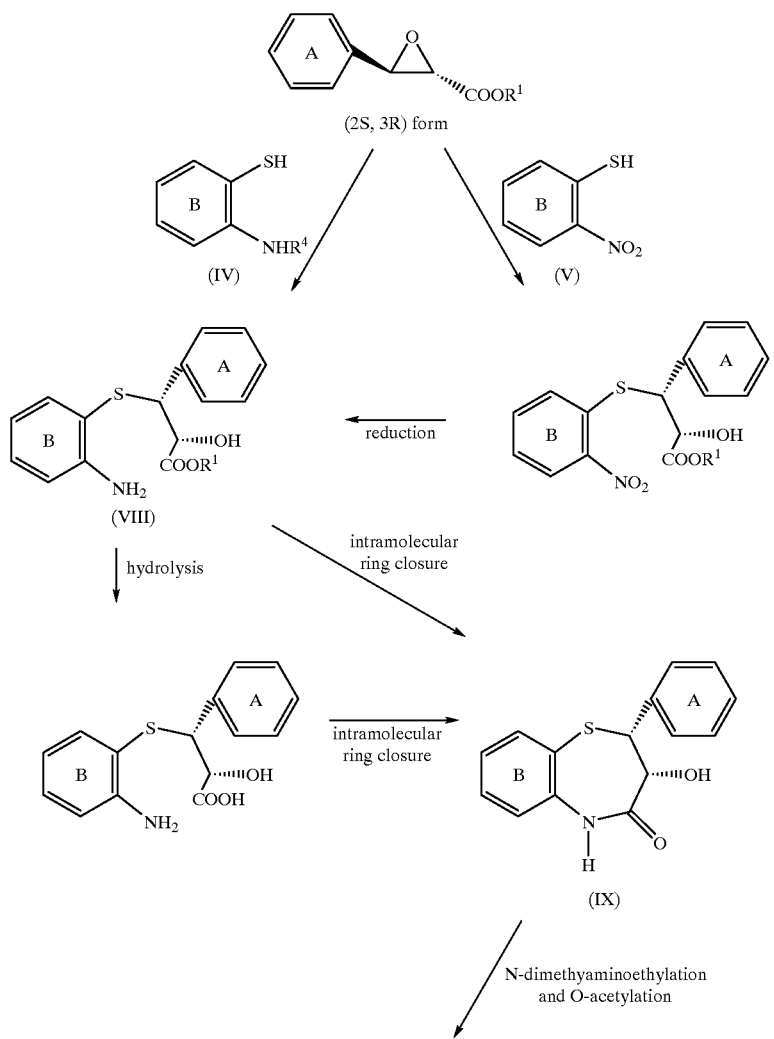

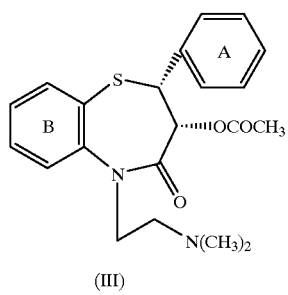

(III)

Examples of the (2R, 3R)-1,5-benzothiazepine derivatives (III) and the pharmaceutically acceptable salts thereof are, for instance, (2R,3R)-cis-2-(4-methylphenyl)-3-acetoxy-5-[2-(dimethylamino)ethyl]-8-methyl-2,3-dihydro-1,5-benzothiazepin-4 (5H)-one and pharmaceutically acceptable salts thereof.

Further, an optically active threo-nitrocarboxylic acid compound of the formula:

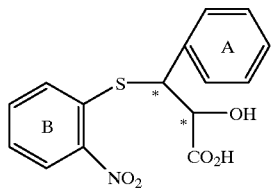

wherein ring A and ring B are as defined above and * denotes asymmetric carbon atoms, which is useful as an optically resolving agent, can be prepared from the optical isomer (A) of trans-3-substituted glycidic acid ester obtained by the process of the present invention.

In the preparation of such optically active threo-nitrocarboxylic acid compounds, the rings A and B are, for example, the same rings as those mentioned in the above-mentioned preparation of 1,5-benzothiazepine derivatives. Preferably, the ring A is a 4-lower alkoxyphenyl group and the ring B is a substituted benzene ring of the formula:

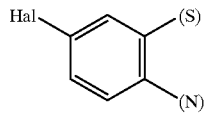

wherein Hal is a halogen atom. More preferably, the ring A is 4-methoxyphenyl group and the ring B is the substituted benzene ring shown by the above formula wherein Hal is chlorine atom.

The preparation of the threo-nitrocarboxylic acid compound can be practiced, for example, by reacting the optical isomer (A) of trans-3-substituted glycidic acid ester with a nitrothiophenol compound of the formula:

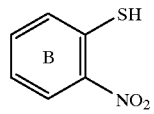

wherein ring B is as defined above, in a manner as disclosed in Japanese Patent Publication Kokoku No. 61-18549, and then hydrolyzing the product according to a method disclosed in Chem. Pharm. Bull., 18(10), 2028–2037(1970).

According to such processes, the (2S,3S)-isomer of the threo-nitrocarboxylic acid compound can be obtained if the (2R,3S)-isomer of the trans-3-substituted glycidic acid ester (I) is used, and the (2R, 3R)-isomer of the threo-nitrocarboxylic acid compound can be obtained if the (2S, 3R) -isomer of the trans-3-substituted glycidic acid ester (I) is used.

Concomitantly, the term "linear or branched lower alkyl group" as used herein means a linear or branched alkyl group having 1 to 6 carbon atoms. Also, the term "linear or branched lower alkoxy group" as used herein means a linear or branched alkoxy group having 1 to 6 carbon atoms. Further, the term "cycloalkyl group" as used herein means a cycloalkyl group having 3 to 6 carbon atoms, and the term "aryl group" as used herein means an aryl group having 6 to 10 carbon atoms.

Also, the term "linear or branched alkyl group" as used herein means a linear or branched alkyl group having 1 to 12 carbon atoms. The term "alkoxyalkyl group" as used herein means an alkoxyalkyl group wherein the alkoxy group has 1 to 6 carbon atoms and the alkyl group has 1 to 6 carbon atoms. Also, the term "arylalkyl group" as used herein means an arylalkyl group wherein the aryl group has 6 to 10 carbon atoms and the alkyl group has 1 to 6 carbon atoms.

The present invention is more specifically described and explained by means of the following Examples. It is to be understood that the present invention is not limited to these Examples.

EXAMPLE 1

In 300 ml eggplant type flask were placed (2R, 3S)-3-(4-methoxyphenyl)glycidic acid methyl ester (hereinafter referred to as "MPGN"), (2S, 3R)-MPGM and (2S, 3R)-MPGR$^3$ [R$^3$ ester of (2R, 3S)-3-(4-methoxyphenyl)glycidic acid, i.e., a compound in which methyl group of (2S, 3R)-MPGM was changed to R$^3$ group; R$^3$=n-propyl group, n-butyl group, n-octyl group, n-decyl group, benzyl group, cyclohexyl group or 2-octyl group] in amounts shown in Table 1 together with 30 ml of methanol. They were dissolved in methanol at an elevated temperature. The solution was cooled to −15° C. with stirring by means of a magnetic stirrer and allowed to stand at −15° C. for 5 minutes. The concentrations of the respective components in the resulting supernatant were measured by HPLC*.

*: HPLC conditions: column, CHIRALCEL OD (Daicel Chemical Co.); Detection, UV at 237; Temp., 40° C.; Flow rate, 1.0 ml/min; Developing solvent, Hexane/Isopropanol=20/1.

From the concentrations, the amounts of the respective components included in the supernatant were estimated. Further, the amount of the crystals was estimated according to the equation: (amount of (2R, 3S)-MPGM before crystallization)−(amount of (2R, 3S)-MPGM in the supernatant).

The results are shown in Table 1.

Small portion of the crystals was obtained by filtration, washed with methanol (−15° C.) in an amount equal to the portion and dried in vacuo, and the purity of the crystals was measured by HPLC. The content of (2R,3S)-MPGM in the crystals was found to be 99% or more in all cases.

stopped. Small portion of the supernatant was taken out and the concentrations of the respective components in the supernatant were measured by HPLC.

From the concentrations, the amounts of the respective components included in the supernatant were estimated.

TABLE 1

| $R^3$ | Composition before crystallization (g) | Amount in supernatant (g) | Amount of crystals deposited (g) |
|---|---|---|---|
| n-Propyl group | (2R,3S)-MPGM: 9.8<br>(2S,3R)-MPGM: 2.0<br>(2S,3R)-MPGR$^3$: 8.3 | (2R,3S)-MPGM: 1.1<br>(2S,3R)-MPGM: no change<br>(2S,3R)-MPGR$^3$: no change | (2R,3S)-MPGM: 8.7 |
| n-Butyl group | (2R,3S)-MPGM: 9.9<br>(2S,3R)-MPGM: 2.7<br>(2S,3R)-MPGR$^3$: 8.5 | (2R,3S)-MPGM: 1.0<br>(2S,3R)-MPGM: no change<br>(2S,3R)-MPGR$^3$: no change | (2R,3S)-MPGM: 8.9 |
| n-Octyl group | (2R,3S)-MPGM: 9.4<br>(2S,3R)-MPGM: 2.2<br>(2S,3R)-MPGR$^3$: 6.7 | (2R,3S)-MPGM: 1.4<br>(2S,3R)-MPGM: no change<br>(2S,3R)-MPGR$^3$: no change | (2R,3S)-MPGM: 8.0 |
| n-Decyl group | (2R,3S)-MPGM: 10.3<br>(2S,3R)-MPGM: 2.8<br>(2S,3R)-MPGR$^3$: 8.6 | (2R,3S)-MPGM: 1.6<br>(2S,3R)-MPGM: no change<br>(2S,3R)-MPGR$^3$: no change | (2R,3S)-MPGM: 8.7 |
| Benzyl group | (2R,3S)-MPGM: 9.6<br>(2S,3R)-MPGM: 2.2<br>(2S,3R)-MPGR$^3$: 7.7 | (2R,3S)-MPGM: 1.6<br>(2S,3R)-MPGM: no change<br>(2S,3R)-MPGR$^3$: no change | (2R,3S)-MPGM: 8.0 |
| Cyclohexyl group | (2R,3S)-MPGM: 9.7<br>(2S,3R)-MPGM: 2.5<br>(2S,3R)-MPGR$^3$: 6.6 | (2R,3S)-MPGM: 1.5<br>(2S,3R)-MPGM: no change<br>(2S,3R)-MPGR$^3$: no change | (2R,3S)-MPGM: 8.2 |
| 2-Octyl group | (2R,3S)-MPGM: 9.3<br>(2S,3R)-MPGM: 2.0<br>(2S,3R)-MPGR$^3$: 5.1 | (2R,3S)-MPGM: 1.4<br>(2S,3R)-MPGM: no change<br>(2S,3R)-MPGR$^3$: no change | (2R,3S)-MPGM: 7.9 |

EXAMPLE 2

In 300 ml eggplant type flask were placed (2R,3S)-MPGM, (2S,3R)-MPGM and (2S,3R)-MPGnBu [(2S,3R)-3-(4-methoxyphenyl)glycidic acid n-butyl ester] in amounts shown in Tables 2 to 7 together with 30 ml of methanol. They were dissolved by stirring the mixture with a 2.5 cm magnetic stirrer at 300 r.p.m. The solution was cooled to a temperature shown in Tables 2 to 7, and after the elapse of a predetermined time (0, 0.5 or 1 hour) the stirring was Further, the amount of the crystals was estimated according to the equation: (amount of (2R, 3S)-MPGM before crystallization)−(amount of (2R,3S)-MPGM in the supernatant).

The clouding time denotes a time until a solution becomes cloudy after reaching the crystallization temperature. The amounts of respective isomers in the supernatant were measured by HPLC with respect to samples taken before occurrence of cloudiness.

TABLE 2

(2S,3R)-MPGnBu/(2S,3R)-MPGM = 1.7 by mole

| Composition before crystallization (g) | Crystallization temperature (° C.) | Clouding time (minute) | Amount in supernatant (g) | Amount of crystals (g) |
|---|---|---|---|---|
| (2R,3S)-MPGM: 10.3<br>(2S,3R)-MPGM: 3.6<br>(2S,3R)-MPGnBu: 7.5 | 10 | >60 | (2R,3S)-MPGM: 2.7<br>(2S,3R)-MPGM: no change<br>(2S,3R)-MPGnBu: no change | (2R,3S)-MPGM: 7.6 |

TABLE 3

(2S,3R)-MPGnBu/(2S,3R)-MPGM = 2.0 by mole

| Composition before crystallization (g) | Crystallization temperature (° C.) | Clouding time (minute) | Amount in supernatant (g) | Amount of crystals (g) |
|---|---|---|---|---|
| (2R,3S)-MPGM: 10.3<br>(2S,3R)-MPGM: 3.4<br>(2S,3R)-MPGnBu: 7.9 | 10 | >60 | (2R,3S)-MPGM: 2.5<br>(2S,3R)-MPGM: no change<br>(2S,3R)-MPGnBu: no change | (2R,3S)-MPGM: 7.8 |

TABLE 4

(2S,3R)-MPGnBu/(2S,3R)-MPGM = 2.2 by mole

| Composition before crystallization (g) | Crystallization temperature (° C.) | Clouding time (minute) | Amount in supernatant (g) | Amount of crystals (g) |
|---|---|---|---|---|
| (2R,3S)-MPGM: 10.3<br>(2S,3R)-MPGM: 3.2<br>(2S,3R)-MPGnBu: 8.3 | 10 | >60 | (2R,3S)-MPGM: 2.2<br>(2S,3R)-MPGM: no change<br>(2S,3R)-MPGnBu: no change | (2R,3S)-MPGM: 8.1 |
| (2R,3S)-MPGM: 10.3<br>(2S,3R)-MPGM: 3.1<br>(2S,3R)-MPGnBu: 8.2 | 0 | 35 | (2R,3S)-MPGM: 1.6<br>(2S,3R)-MPGM: no change<br>(2S,3R)-MPGnBu: no change | (2R,3S)-MPGM: 8.7 |
| (2R,3S)-MPGM: 10.3<br>(2S,3R)-MPGM: 3.1<br>(2S,3R)-MPGnBu: 8.2 | −10 | 5 | (2R,3S)-MPGM: 0.9<br>(2S,3R)-MPGM: no change<br>(2S,3R)-MPGnBu: no change | (2R,3S)-MPGM: 9.4 |

TABLE 5

(2S,3R)-MPGnBu/(2S,3R)-MPGM = 2.4 by mole

| Composition before crystallization (g) | Crystallization temperature (° C.) | Clouding time (minute) | Amount in supernatant (g) | Amount of crystals (g) |
|---|---|---|---|---|
| (2R,3S)-MPGM: 10.4<br>(2S,3R)-MPGM: 3.0<br>(2S,3R)-MPGnBu: 8.7 | 10 | >60 | (2R,3S)-MPGM: 2.2<br>(2S,3R)-MPGM: no change<br>(2S,3R)-MPGnBu: no change | (2R,3S)-MPGM: 8.2 |
| (2R,3S)-MPGM: 10.3<br>(2S,3R)-MPGM: 2.9<br>(2S,3R)-MPGnBu: 8.4 | 0 | 55 | (2R,3S)-MPGM: 2.0<br>(2S,3R)-MPGM: no change<br>(2S,3R)-MPGnBu: no change | (2R,3S)-MPGM: 8.3 |
| (2R,3S)-MPGM: 10.3<br>(2S,3R)-MPGM: 2.9<br>(2S,3R)-MPGnBu: 8.4 | −10 | 50 | (2R,3S)-MPGM: 1.1<br>(2S,3R)-MPGM: no change<br>(2S,3R)-MPGnBu: no change | (2R,3S)-MPGM: 9.2 |

TABLE 6

(2S,3R)-MPGnBu/(2S,3R)-MPGM = 2.7 by mole

| Composition before crystallization (g) | Crystallization temperature (° C.) | Clouding time (minute) | Amount in supernatant (g) | Amount of crystals (g) |
|---|---|---|---|---|
| (2R,3S)-MPGM: 10.3<br>(2S,3R)-MPGM: 2.7<br>(2S,3R)-MPGnBu: 8.7 | 10 | >60 | (2R,3S)-MPGM: 2.3<br>(2S,3R)-MPGM: no change<br>(2S,3R)-MPGnBu: no change | (2R,3S)-MPGM: 8.0 |
| (2R,3S)-MPGM: 10.3<br>(2S,3R)-MPGM: 2.7<br>(2S,3R)-MPGnBu: 8.7 | 0 | >60 | (2R,3S)-MPGM: 1.4<br>(2S,3R)-MPGM: no change<br>(2S,3R)-MPGnBu: no change | (2R,3S)-MPGM: 8.9 |
| (2R,3S)-MPGM: 10.3<br>(2S,3R)-MPGM: 2.7<br>(2S,3R)-MPGnBu: 8.7 | −10 | 55 | (2R,3S)-MPGM: 0.8<br>(2S,3R)-MPGM: no change<br>(2S,3R)-MPGnBu: no change | (2R,3S)-MPGM: 9.5 |

TABLE 7

(2S,3R)-MPGnBu/(2S,3R)-MPGM = 3.8 by mole

| Composition before crystallization (g) | Crystallization temperature (° C.) | Clouding time (minute) | Amount in supernatant (g) | Amount of crystals (g) |
|---|---|---|---|---|
| (2R,3S)-MPGM: 10.3<br>(2S,3R)-MPGM: 2.0<br>(2S,3R)-MPGnBu: 9.2 | 0 | >60 | (2R,3S)-MPGM: 1.4<br>(2S,3R)-MPGM: no change<br>(2S,3R)-MPGnBu: no change | (2R,3S)-MPGM: 7.6 |
| (2R,3S)-MPGM: 10.3<br>(2S,3R)-MPGM: 2.0<br>(2S,3R)-MPGnBu: 9.2 | −10 | >60 | (2R,3S)-MPGM: 0.8<br>(2S,3R)-MPGM: no change<br>(2S,3R)-MPGnBu: no change | (2R,3S)-MPGM: 9.5 |

EXAMPLE 3

In 1,000 ml eggplant type flask were placed (2R,3S)-MPGM, (2S,3R)-MPGM and (2S,3R)-MPGnBu in amounts shown in Table 8 together with an amount of a solvent shown in Table 8. They were dissolved in the solvent by stirring the mixture with a 2.5 cm magnetic stirrer at 300 r.p.m. The solution was cooled to a temperature shown in Table 8, and immediately the stirring was stopped. Small portion of the supernatant was taken out and the concentrations of the respective components in the supernatant were measured by HLPC.

From the concentrations, the amounts of the respective components included in the supernatant were estimated. Further, the amount of the crystals was estimated according to the equation: (amount of (2R, 3S)-MPGM prior to crystallization)−(amount of (2R, 3S)-MPGM in the supernatant). The results are shown in Table 8.

Small portion of the crystals was obtained by filtration, washed with methanol (−0° C.) in an amount equal to the portion and dried in vacuo, and the purity of the crystals was measured by the use of HPLC. The content of (2R,3S)-MPGM in the crystals was found to be 99% or more in all cases.

EXAMPLE 4

In 300 ml eggplant type flask were placed (2R,3S)-MPGM, (2S,3R)-MPGM and (2S,3R)-MPGnBu in amounts shown in Table 9 together with methanol of an amount shown in Table 9. They were dissolved in methanol by stirring the mixture with a 2.5 cm magnetic stirrer at 300 r.p.m. The solution was cooled to −10° C. . After stirring at that temperature for 1 hour, immediately the stirring was stopped. Small portion of the supernatant was taken out and the concentrations of the respective components in the supernatant were measured by HLPC.

From the concentrations, the amounts of the respective components included in the supernatant were estimated. Moreover, the crystals were obtained by filtration, washed with methanol (−10C) in an amount equal to the crystals and dried in vacuo, and the composition of the crystals was measured by HPLC. The results are shown in Table 9.

TABLE 8

| Crystallization solvent | Amount of solvent (ml) | Crystallization temperature (° C.) | Composition before crystallization (g) | Amount in supernatant (g) | Amount of crystals (g) |
| --- | --- | --- | --- | --- | --- |
| Xylene | 100 | −10 | (2R,3S)-MPGM: 49<br>(2S,3R)-MPGM: 14<br>(2S,3R)-MPGnBu: 39 | (2R,3S)-MPGM: 9<br>(2S,3R)-MPGM: no change<br>(2S,3R)-MPGnBu: no change | (2R,3S)-MPGM: 40 |
| Toluene | 100 | −10 | (2R,3S)-MPGM: 49<br>(2S,3R)-MPGM: 14<br>(2S,3R)-MPGnBu: 39 | (2R,3S)-MPGM: 9<br>(2S,3R)-MPGM: no change<br>(2S,3R)-MPGnBu: no change | (2R,3S)-MPGM: 40 |
| Isopropyl ether | 100 | −10 | (2R,3S)-MPGM: 49<br>(2S,3R)-MPGM: 14<br>(2S,3R)-MPGnBu: 39 | (2R,3S)-MPGM: 8<br>(2S,3R)-MPGM: no change<br>(2S,3R)-MPGnBu: no change | (2R,3S)-MPGM: 41 |
| t-Butyl methyl ether | 150 | −10 | (2R,3S)-MPGM: 49<br>(2S,3R)-MPGM: 14<br>(2S,3R)-MPGnBu: 39 | (2R,3S)-MPGM: 9<br>(2S,3R)-MPGM: no change<br>(2S,3R)-MPGnBu: no change | (2R,3S)-MPGM: 40 |
| Isopropanol | 150 | 3 | (2R,3S)-MPGM: 49<br>(2S,3R)-MPGM: 14<br>(2S,3R)-MPGnBu: 39 | (2R,3S)-MPGM: 8<br>(2S,3R)-MPGM: no change<br>(2S,3R)-MPGnBu: no change | (2R,3S)-MPGM: 41 |
| Ethanol | 150 | −10 | (2R,3S)-MPGM: 50<br>(2S,3R)-MPGM: 14<br>(2S,3R)-MPGnBu: 42 | (2R,3S)-MPGM: 6<br>(2S,3R)-MPGM: no change<br>(2S,3R)-MPGnBu: no change | (2R,3S)-MPGM: 44 |

TABLE 9

| Amount solvent (ml) | Crystallization temperature (° C.) | Composition before crystallization (g) | Amount in supernatant (g) | Amount of crystals obtained (g) | Composition of crystals (% by mole) |
| --- | --- | --- | --- | --- | --- |
| 30 | −10 | (2R,3S)-MPGM: 10.0<br>(2R,3R)-MPGM: 2.5<br>(2R,3R)-MPGnBu: 9.3 | (2R,3S)-MPGM: 0.8<br>(2R,3R)-MPGM: no change<br>(2R,3R)-MPGnBu: no change | 8.5 | (2R,3S)-MPGM: 99.8<br>(2R,3R)-MPGM: 0.1<br>(2R,3R)-MPGnBu: 0.1 |
| 20 | −10 | (2R,3S)-MPGM: 10.0<br>(2R,3R)-MPGM: 2.5<br>(2R,3R)-MPGnBu: 9.3 | (2R,3S)-MPGM: 0.7<br>(2R,3R)-MPGM: no change<br>(2R,3R)-MPGnBu: no change | 9.2 | (2R,3S)-MPGM: 99.2<br>(2R,3R)-MPGM: 0.3<br>(2R,3R)-MPGnBu: 0.5 |

EXAMPLE 5

In 300 ml eggplant type flask were placed (2R, 3S)-MPGM, (2S, 3R)-MPGM, (2R, 3S)-MPGnBu and (2S, 3R)-MPGnBu in amounts shown in Table 10 together with 30 ml of methanol. They were dissolved in methanol by stirring the mixture with a 2.5 cm magnetic stirrer at 300 r.p.m. The solution was cooled to −15° C. over 30 minutes. After further stirring at that temperature for 2 hours, the stirring was stopped, and small portion of the supernatant was taken out and the concentrations of the respective components in the supernatant were measured by HLPC.

From the concentrations, the amounts of the respective components included in the supernatant were estimated. Further, the amount of the crystals was estimated according to the equation: (amount of (2R, 3S)-MPGM prior to crystallization)−(amount of (2R, 3S)-MPGM in the supernatant).

Moreover, the crystals were obtained by filtration, washed with methanol (−15° C. ) in an amount equal to the crystals and dried in vacuo, and the composition of the crystals was measured by HPLC. The results are shown in Table 10.

TABLE 10

| (2R,3S)-MPGnBu / (2R,3S)-MPGM | (molar ratio) | Composition before crystallization (g) | Amount of crystals deposited (g) | Composition of crystals (% by mole) |
|---|---|---|---|---|
| 0.01 | | (2R,3S)-MPGM: 9.9 | (2R,3S)-MPGM: 8.9 | (2R,3S)-MPGM: 99.7 |
| | | (2S,3R)-MPGM: 2.7 | | (2S,3R)-MPGM: 0.1 |
| | | (2R,3S)-MPGnBu: 0.1 | | (2R,3S)-MPGnBu: 0.1 |
| | | (2S,3R)-MPGnBu: 8.5 | | (2S,3R)-MPGnBu: 0.1 |
| 0.10 | | (2R,3S)-MPGM: 8.1 | (2R,3S)-MPGM: 6.5 | (2R,3S)-MPGM: 96.1 |
| | | (2S,3R)-MPGM: 2.1 | | (2S,3R)-MPGM: 0.5 |
| | | (2R,3S)-MPGnBu: 1.0 | | (2R,3S)-MPGnBu: 2.5 |
| | | (2S,3R)-MPGnBu: 5.5 | | (2S,3R)-MPGnBu: 0.9 |
| 0.25 | | (2R,3S)-MPGM: 7.6 | (2R,3S)-MPGM: 6.0 | (2R,3S)-MPGM: 96.6 |
| | | (2S,3R)-MPGM: 2.1 | | (2S,3R)-MPGM: 0.2 |
| | | (2R,3S)-MPGnBu: 2.3 | | (2R,3S)-MPGnBu: 2.9 |
| | | (2S,3R)-MPGnBu: 7.1 | | (2S,3R)-MPGnBu: 0.3 |
| 0.50 | | (2R,3S)-MPGM: 6.5 | (2R,3S)-MPGM: 5.0 | (2R,3S)-MPGM: 93.8 |
| | | (2S,3R)-MPGM: 1.7 | | (2S,3R)-MPGM: 0.2 |
| | | (2R,3S)-MPGnBu: 3.8 | | (2R,3S)-MPGnBu: 5.5 |
| | | (2S,3R)-MPGnBu: 9.0 | | (2S,3R)-MPGnBu: 0.5 |

EXAMPLE 6

A solution of 10.4 g of (2R,3S)-MPGM, 10.4 g of (2S,3R)-MPGM and 40.5 g of (2S,3R)-MPGnBu in 150 ml of methanol was placed in a 500 ml eggplant flask and was stirred at 300 r.p.m. by a 2.5 cm magnetic stirrer. The solution was cooled to −10° C. over 30 minutes and further stirred for 10 minutes. The crystals were obtained by filtration, washed with 10 ml of methanol (−10° C. ) and dried in vacuo. The composition of the crystals was measured by HPLC. The content of (2R, 3S)-MPGM in 4.5 g of crystals (yield of 43% based on the amount of (2R, 3S)-MPGM prior to the crystallization) was found to be 99% or more.

After obtaining the crystals, 10 ml of methanol, which corresponds to the washing liquid in the mixture of the filtrate and the washings, was distilled away.

The concentrated mixture was cooled to −10° C., and thereto were added seed crystals of (2S, 3R)-MPGM. When the mixture was stirred at that temperature for 30 minutes, it became cloudy and an amorphous-like material precipitated.

The amorphous-like material was obtained by filtration and the composition thereof was measured by HPLC. It was found that the amorphous-like material is a solid containing (2S, 3R)-MPGM having the same configuration as the seed crystals in the largest amount together with almost the same amount of (2R, 3S)-MPGM and about two-third amount of (2S,3R)-MPGnBu.

EXAMPLE 7

In a mixed solvent of 500 ml of xylene, 80 ml of n-butanol and 0.25 ml of water was dissolved 104 g (0.5 mole) of (2RS,3SR)-MPGM [52 g of (2R,3S)-MPGM and 52 g of (2S, 3R)-MPGM]. In the resulting solution was suspended 200 mg of esterase derived from Serratia marcescens (olive oil hydrolysis activity: 4×10$^4$U) which was obtained in Reference Example 1-(2-b) described after. The solution was stirred at 30° C. for 24 hours, and the reaction mixture was analyzed by HPLC. It was found that the product was composed of 50 g of (2R,3S)-MPGM, 13.5 g of (2S,3R)-MPGM and 44 g of (2S,3R)-MPGnBu. The enzyme was removed from the reaction mixture by filtration, and the whole solvent was distilled away from the filtrate under reduced pressure to give an oily residue. To the residue was added 150 ml of methanol, and it was stirred for crystallization. In order to further raise the yield, the mixture was cooled to −15° C. and stirred at the same temperature for 30 minutes. The crystals were obtained by filtration, washed with 40 ml of methanol (-15° C. ) and dried in vacuo to give 44.2 g of (2R,3S)-MPGM.

From the analysis of the filtrate obtained at that time, it was also found that the mother liquor contained 6 g of (2R,3S)-MPGM, 13.5 g of (2S,3R)-MPGM and 44 g of (2S, 3R)-MPGnBu. The yield of the crystals was 85.0% (percentage on the basis that (2R,3S)-MPGM in the charged racemic compound was 100%). The content of (2R, 3S)-MPGM in the crystals was found to be 99% or more.

EXAMPLE 8

20.8 g of (2RS,3SR)-MPGM [10.4 g of (2R,3S)-MPGM and 10.4 g of (2S,3R)-MPGM], 100 ml of xylene, 16 ml of n-butanol, 25 μl of water and 10 mg of esterase derived from *Serratia marcescens* (olive oil hydrolysis activity: 2×10$^3$U) which was obtained in Reference Example 1-(2-b) described after were mixed. The mixture was subjected to an enzymatic transesterification reaction at 30° C. until reaching the transesterification conversion shown in Table 11. The enzyme was removed from the reaction mixture by filtration, and the whole solvent was distilled away from the filtrate at a temperature of 60 to 70° C. under a reduced pressure to give an oily residue.

To the residue was added 30 ml of methanol, and it was stirred in an eggplant type flask at 300 r.p.m. with a 2.5 cm magnetic stirrer. After cooling the mixture to −10° C., the stirring was stopped. Small portion of the supernatant was taken out and the concentrations of the components in the supernatant were measured by HLPC. From the concentrations, the amounts of the compounds included in the supernatant were estimated.

Further, the amount of the crystals was estimated according to the equation: (amount of (2R,3S)-MPGM prior to crystallization)−(amount of (2R, 3S)-MPGM in the supernatant). The results are shown in Table 11.

Small portion of the crystals was obtained by filtration, washed with methanol of −10° C. in an amount equal to the crystals, dried in vacuo and analyzed by HPLC. The content of (2R, 3S)-MPGM in the crystals was found to be 99% or more in all cases.

From the analysis of the filtrate obtained at that time, it was also found that the mother liquor contained 7 g of (2R,3S)-MPGM, 14.7 g of (2S,3R)-MPGM and 38 g of (2S,3R)-MPGnBu. The yield of the crystals was 82.9% (percentage on the basis that (2R,3S)-MPGM in the charged racemic compound was 100%). The content of (2R,3S)-MPGM in the crystals was found to be 99% or more.

EXAMPLE 10

(1) In 150 ml of methanol were dissolved 20 g of (2RS,3SR)-MPGM and 41 g of (2S,3R)-MPGnBu at a temperature of 30 to 40C. The solution was cooled with stirring, and 10 mg of seed crystals of (2R,3S)-MPGM was added to the solution at 0° C. The solution was further cooled to −10° C. over 30 minutes and was stirred at that temperature for 10 minutes. The crystals were obtained by filtration with a glass filter, washed with 20 ml of methanol

TABLE 11

| Conversion | Composition before crystallization (g) | Amount in supernatant (g) | Amount of crystals deposited (g) |
|---|---|---|---|
| 0.36 | (2R,3S)-MPGM: 10.2<br>(2S,3R)-MPGM: 3.1<br>(2R,3S)-MPGnBu: 0.03<br>(2S,3R)-MPGnBu: 8.2 | (2R,3S)-MPGM: 0.9<br>(2S,3R)-MPGM: no change<br>(2R,3S)-MPGnBu: no change<br>(2S,3R)-MPGnBu: no change | (2R,3S)-MPGM: 9.3 |
| 0.37 | (2R,3S)-MPGM: 10.2<br>(2S,3R)-MPGM: 2.9<br>(2R,3S)-MPGnBu: 0.03<br>(2S,3R)-MPGnBu: 8.3 | (2R,3S)-MPGM: 1.1<br>(2S,3R)-MPGM: no change<br>(2R,3S)-MPGnBu: no change<br>(2S,3R)-MPGnBu: no change | (2R,3S)-MPGM: 9.1 |
| 0.38 | (2R,3S)-MPGM: 10.2<br>(2S,3R)-MPGM: 2.7<br>(2R,3S)-MPGnBu: 0.03<br>(2S,3R)-MPGnBu: 8.6 | (2R,3S)-MPGM: 0.8<br>(2S,3R)-MPGM: no change<br>(2R,3S)-MPGnBu: no change<br>(2S,3R)-MPGnBu: no change | (2R,3S)-MPGM: 9.4 |
| 0.41 | (2R,3S)-MPGM: 10.2<br>(2S,3R)-MPGM: 2.0<br>(2R,3S)-MPGnBu: 0.03<br>(2S,3R)-MPGnBu: 9.2 | (2R,3S)-MPGM: 0.8<br>(2S,3R)-MPGM: no change<br>(2R,3S)-MPGnBu: no change<br>(2S,3R)-MPGnBu: no change | (2R,3S)-MPGM: 9.4 |

EXAMPLE 9

In a mixed solvent of 500 ml of xylene and 80 ml of n-butanol was dissolved 104 g (0.5 mole) of (2RS,3SR)-MPGM [52 g of (2R,3S)-MPGM and 52 g of (2S, 3R)-MPGM]. In the resulting solution was suspended 3.0 g of esterase immobilized on Celite (olive oil hydrolysis activity: 2.5×10$^4$U) which was obtained in Reference Example 1-(2-a) described after. The solution was stirred at 30° C. for 24 hours, and the reaction mixture was analyzed by HPLC. It was found that the product was composed of 51 g of (2R,3S)-MPGM, 14.7 g of (2S,3R)-MPGM and 38 g of (2S,3R)-MPGBu. The Celite-immobilized esterase was removed from the reaction mixture by filtration, and the whole solvent was distilled away from the filtrate at a temperature of 60 to 70° C. under reduced pressure to give an oily residue. To the residue was added 150 ml of methanol, and it was stirred for crystallization. In order to further raise the yield, the mixture was cooled to −10° C. and stirred at the same temperature for 30 minutes. The crystals were obtained by filtration, washed with 40 ml of methanol of -10C and dried in vacuo to give 43.1 g of (2R,3S)-MPGM.

of −10° C. and dried under vacuum to give (2R, 3S)-MPGM. The filtrate and washings were combined to give a methanol solution containing (2R,3S)-MPGM, (2S,3R)-MPGM and (2S,3R)-MPGnBu.

(2) To the above methanol solution were added 100 ml of methanol and 10 ml of diisopropylamine. The solution was stirred at 30° C. for 16 hours to convert (2S,3R)-MPGnBu into (2S,3R)-MPGM.

(3) The reaction mixture obtained in the step (2) was allowed to stand at 0° C. for 30 minutes. The crystals of (2S,3R)-MPGM were obtained by filtration and washed with 40 ml of methanol of 5° C. The filtrate was concentrated under reduced pressure to give a residue containing (2S, 3R)-MPGM and (2R, 3S)-MPGM in approximately equal amounts.

(4) To the residue was added (2RS,3SR)-MPGM so that the total amount of (2RS, 3SR)-MPGM became about 20 g. Thereto were further added (2S, 3R)-MPGnBu and methanol. The resulting solution was applied to the above step (1). The procedure consisting of the steps (1) to (4) was repeated three times, and the results thereof are shown in Table 12.

TABLE 12

(Change in composition of components in methanol solution)

| Procedure | (2R,3S)-MPGM (g) | (2S,3R)-MPGM (g) | (2S,3R)-MPGnBu (g) |
|---|---|---|---|
| Addition of racemic compound | 10(+10 addition) | 10(+10 addition) | 41(+41 addition) |
| Crystallization | 4.4(−5.6 deposition) | 10 | 41 |
| Chemical transesterification | 4.4 | 44 (+34.1 transesterification −0.1*) | 0(−41 transesterification) |
| Crystallization | 3.6(−0.8***) | 3.9(−37.9 deposition −2.2**) | 0 |
| Addition of racemic compound | 10(+6.4 addition) | 10.3(+6.4 addition) | 41(+41 addition) |
| Crystallization | 4.2 (−5.8 deposition) | 10.3 | 41 |
| Chemical transesterification | 4.2 | 44(+34.1 transesterification −0.4*) | 0(−41 transesterification) |
| Crystallization | 4.2 | 4.4(−35.8 deposition −3.8**) | 0 |
| Addition of racemic compound | 10(+5.8 addition) | 10.2(+5.8 addition) | 41(+41 addition) |
| Crystallization | 5.2(−4.8 deposition) | 10.2 | 41 |
| Chemical transesterification | 5.2 | 44 (+34.1 transesterification −0.3*) | 0(−41 transesterification) |
| Crystallization | 5.2 | 6.2(−37.0 deposition −0.8**) | 0 |

*Loss at the time of transesterification
**Loss at the time of washing crystals
***Loss caused by washing and so on There was obtained 16.2 g of (2R,3S)-MPGM in total by the above three cycle procedure. The purity and optical purity of (2R,3S)-MPGM obtained in each cycle were 98% or more and 97% or more, respectively.

Since (2S,3R)-MPGM can be obtained as crystals in a larger, molar amount than (2S,3R)-MPGnBu used as an ester compound, it is also possible to obtain (2S, 3R)-MPGM having high purity if thus-obtained (2S, 3R)-MPGM is chemically transesterified to (2S, 3R)-MPGnBu only in an amount necessary for (2S, 3R)-MPGnBu in the next cycle.

EXAMPLE 11

In a 2 liter reactor equipped with a stirrer, 187 g (0.9 mole) of (2RS,3SR)-MPGM [93.5 g of (2R,3S)-MPGM and 93.5 g of (2S,3R)-MPGM] was dissolved in a mixed solvent of 720 ml of xylene and 57.6 ml (0.9 mole) of n-butanol. In the resulting solution was suspended 3.0 g of Celite-immobilized esterase (to which 0.81 ml of purified water was previously added and which had an olive oil hydrolysis activity of $2.5 \times 10^4$ U) which was obtained in Reference Example 1-(2-a) described after. The solution was stirred at 30° C. for 4 hours under a reduced pressure of 15 mmHg, and the reaction mixture was analyzed by HPLC. It was found that the product was composed of 91.6 g of (2R,3S)-MPGM, 24.3 g of (2S,3R)-MPGM and 83.2 g of (2S,3R)-MPGnBu.

The Celite-immobilized esterase was removed from the reaction mixture by filtration, and the filtrate was concentrated at a temperature of 60 to 70° C. under reduced pressure to give an oily residue. To the residue was added 150 ml of methanol, and it was cooled to −10° C. with stirring and further stirred at that temperature for 30 minutes. The crystals were obtained by filtration, washed with methanol of −10° C. and dried in vacuo to give 82.3 g of (2R, 3S)-MPGM. The mother liquor and washings were combined and analyzed by HPLC. It was found that the mixture contained 9.1 g of (2R,3S)-MPGM, 24.1 g of (2S,3R)-MPGM and 83.0 g of (2S,3R)-MPGnBu.

REFERENCE EXAMPLE 1

(1) In a 30 liter jar fermenter was placed 18 liters of a liquid medium of pH 7.0 containing 1% of dextrin, 0.2% of ammonium sulfate, 2% of Meast S (made by Asahi Breweries, Ltd.), 0.2% of potassium dihydrogenphosphate, 0.05% of magnesium sulfate, 0.001% of ferrous sulfate, 1.5 w/v % of a sorbitane trioleate surfactant (Rheodol SP-030, made by Kao Corporation) and 0.2 v/v % of a polyalkylene glycol derivative surfactant (trade mark Kararin 102, made by Sanyo Chemical Industries, Ltd.). After sterilizing the medium, 200 ml of a pre-cultured broth of Serratia marcescens Sr41 FERM BP-487 obtained by previously culturing with reciprocal shaking at 27.5° C. for 20 hours in the same culture medium as above was inoculated into the sterilized medium. The mixture was cultured at 25° C. for 28 hours with continuously adding 1.5% of L-proline to the medium under the conditions of 0.33 vvm, 0.5 kg/cm$^2$·G and 300 r.p.m. Ten liters of the culture broth was centrifuged to remove the cells, and impurities were removed from the supernatant by the use of an adsorptive resin SP207 (made by Mitsubishi Chemical Corporation). The thus obtained supernatant was concentrated to 1 liter by using a ultrafiltration membrane (SLP1053 made by Asahi Chemical Industry Co., Ltd.) to give 1,080 ml of a concentrated liquid of esterase having an olive oil hydrolysis activity of $1.0 \times 10^4$ U/ml.

(2-a) After impregnating 30 ml of the concentrated enzyme liquid obtained in (1) into 30 g of Celite (made by Celite Corporation, California, U.S.A.) placed in a 500 ml eggplant type flask, they were uniformly mixed and dried at an external temperature of 30° C. under reduced pressure by using a rotary evaporator to give 36.5 g of Celite-immobilized esterase having an activity of 8.2 U/mg.

(2-b) Lyophilized was 1,000 ml of the concentrated enzyme liquid obtained in (1) to give 54 g of esterase having an olive oil hydrolysis activity of $1.96 \times 10^5$ U/g.

REFERENCE EXAMPLE 2

A mixture of 225 ml of a 2% aqueous solution of polyvinyl alcohol (trade mark Poval 117, made by Kuraray Co., Ltd.) and 75 ml of olive oil was stirred at a temperature of 5 to 10° C. for 10 minutes at 14,500 r.p.m. to form an emulsion. Then, 5.0 ml of the obtained olive oil emulsion and 4.0 ml of a 0.25 M tris-HCl buffer (pH8.0, containing 2.5 mM of calcium chloride) were pre-heated at 37° C. for 10 minutes, and thereto was added 1 ml of an enzyme liquid. The reaction was conducted at 37° C. for 20 minutes, and 20 ml of an acetone-ethanol mixed solvent (1:1) was added to the reaction mixture to terminate the reaction. The reaction mixture was titrated with a 0.05 N NaOH solution using phenolphthalein as the indicator. The amount of enzyme which liberated 1 μmole of a fatty acid per minute by the above procedure was defined as one unit (U).

As explained above, according to the present invention, from a solution containing a mixture of optical isomers of trans-3-substituted glycidic acid esters, a desired optical isomer having high purity can be crystallized until the concentration of the desired optical isomer in the mother liquor becomes very low as compared with conventional processes.

Further, after asymmetrically and enzymatically transesterifying racemic trans-3-substituted glycidic acid esters, a desired optical isomer having high purity can be crystallized from the reaction mixture until the concentration of the desired optical isomer in the mother liquor becomes very low as compared with conventional processes.

What we claim is:

1. In a process for preparing a (2S,3S)-1,5-benzothiazepine derivative of the formula (II):

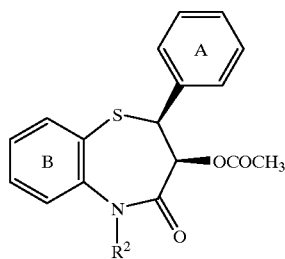

(II)

wherein ring A and ring B are independently a substituted or unsubstituted benzene ring, and $R^2$ is a 2-(dimethylamino)ethyl group or a group of the formula:

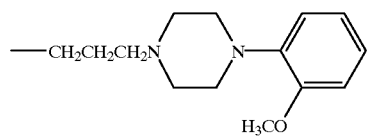

or a pharmaceutically acceptable salt thereof, the improvement comprising using as the starting material a (2R,3S)-isomer of trans-3-substituted glycidic acid ester compound of the formula (I):

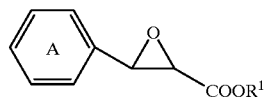

(I)

wherein ring A is a substituted or unsubstituted benzene ring, and $R^1$ is an ester residue, which is obtained by
preparing a solution of the (2R,3S)-isomer (A) and the (2S,3R)-isomer (B) of the ester compound (I), both of which are optical isomers due to the asymmetric carbons at the 2- and 3-positions, and an ester compound (B') which is different from the (2S,3R)-isomer (B) only in the ester residue $R^1$, crystallizing the (2R,3S)-isomer (A) from the solution up to the extent that the (2R,3S)-isomer (A) is crystallized without the precipitation of the (2S,3R)-isomer (B) due to the presence of the ester compound (B') though the (2S,3R)-isomer (B) would precipitate if the ester compound (B') were not present, and
isolating the crystals of the (2R,3S)-isomer (A).

2. A process for preparing a (2S,3S)-isomer of a 1,5-benzothiazepine derivative of the formula (II):

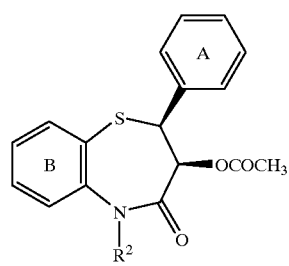

(II)

wherein ring A and ring B are independently a substituted or unsubstituted benzene ring, and $R^2$ is a 2-(dimethylamino)ethyl group or a group of the formula:

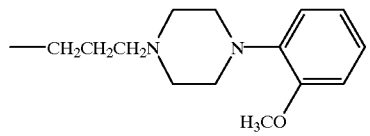

or a pharmaceutically acceptable salt thereof, which comprises (1) obtaining the (2R,3S)-isomer of a trans-3-substituted glycidic acid ester compound of the formula (I):

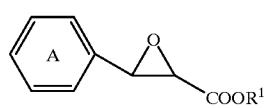

(I)

wherein ring A is a substituted or unsubstituted benzene ring, and $R^1$ is an ester residue by
preparing a solution of the (2R,3S)-isomer (A) and the (2S,3R)-isomer (B) of the ester compound (I) and an ester compound (B') which is different from the (2S,3R)-isomer (B) only in the ester residue $R^1$, crystallizing the (2R,3S)-isomer (A) from the solution up to the extent that the (2R,3S)-isomer (A) is crystallized without the precipitation of the (2S,3R)-isomer (B) due to the presence of the ester compound (B') though the (2S,3R)-isomer (B) would precipitate if the ester compound (B') were not present, and
isolating the crystals of the (2R,3S)-isomer (A), and (2) converting the (2R,3S)-isomer (A) to the (2S,3S)-isomer of the 1,5-benzothiazepine derivative or a pharmaceutically acceptable salt thereof.

3. The process of claim 1 or 2, wherein the solution further contains a small amount of an ester compound (A') which is different from the (2R,3S)-isomer (A) only in the ester residue $R^1$ and has the same ester residue as the ester compound.

4. The process of claim 3, wherein the ester residue of the (2S,3R)-isomer (B) is a methyl or an ethyl group, and the ester residue of the ester compound (B') is a member selected from the group consisting of:
(a) a linear or branched alkyl group which has more carbon atoms that that of the ester residue $R^1$ of the (2S,3R)-isomer (B) and which may be substituted by a halogen atom;
(b) an alkoxyalkyl group which may be substituted by a halogen atom, and
(c) an arylalkyl group which may be substituted by a linear or branched lower alkyl group, a linear or branched lower alkoxy group or a halogen atom.

5. The process of claim 1 or 2, wherein the molar ratio of (2R,3S)-isomer (A)/(2S,3R)-isomer (B) in the solution is from 4/6 to 10/1, and the molar ratio of ester compound (B')/(2S,3R)-isomer (B) in the solution is from 5/3 to 10/1.

6. The process of claim 3, wherein the molar ratio of ester compound (A')/(2R/3S)-isomer (A) is at most 9/35 of that of ester compound (B')/(2S/3R)-isomer (B).

7. The process of claim 1 or 2, wherein the solvent of the solution is a member selected from the group consisting of an alcohol solvent, an ether solvent, an aromatic hydrocarbon solvent which may be substituted by a halogen atom, an aliphatic hydrocarbon solvent which may be substituted by a halogen atom and an ester solvent.

8. The process of claim 1 or 2, wherein the concentration of (2R,3S)-isomer (A) in the solution prior to crystallizing is from 0.5 to 4 moles/liter, and the crystallization is carried out at a temperature of −30 to +15° C.

9. The process of claim 1 or 2, wherein the solution to be subjected to the crystallization is a solution obtained by transesterifying the (2S,3R)-isomer (B) in the solution of the (2R,3S)-isomer (A) and the (2S,3R)-isomer (B) to an ester compound (B') in the presence of an enzyme having a stereoselective transesterification ability by the use of an alcohol.

10. The process of claim 9, wherein the enzyme has an E-value of at least 20 measured when the conversion rate of transesterification reaction is 10%.

11. The process of claim 9, wherein the transesterification is conducted so that the molar ratio of ester compound (B')/(2S,3R)-isomer (B) is from 5/3 to 10/1.

12. The process of claim 1 or 2, wherein ring A is a 4-methoxyphenyl group, the ester residue of the (2S,3R)-isomer (B) is a methyl group, and the ester residue of the ester compound (B') is a n-butyl group.

13. The process of claim 12, wherein ring B is an unsubstituted benzene ring, and $R^2$ is a 2-(dimethylamino) ethyl group.

14. In a process for preparing a (2S,3S)-1,5-benzothiazepine derivative of the formula (II):

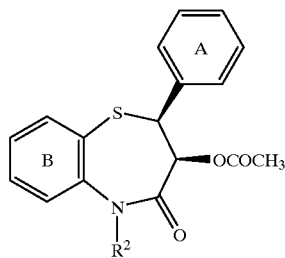

(II)

wherein ring A and ring B are independently a substituted or unsubstituted benzene ring, and $R^2$ is a 2-(dimethylamino)

ethyl group or a group of the formula:

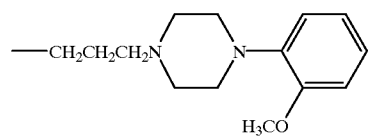

or a pharmaceutically acceptable salt thereof, the improvement comprising using as the starting material a (2R,3S)-isomer of a trans-3-substituted glycidic acid ester compound of the formula (I):

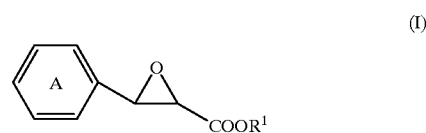

(I)

wherein ring A is a substituted or unsubstituted benzene ring, and $R^1$ is an ester residue, which is obtained by subjecting a mixture of (2R,3S)-isomer (A) and (2S,3R)-isomer (B) of the ester compound (I), both of which are optical isomers due to the asymmetric carbons at the 2- and 3-positions, to transesterification in the presence of an alcohol and an enzyme having a stereoselective transesterification ability, thereby transesterifying the (2S,3R)-isomer (B) with the alcohol to produce an ester compound (B') which is different from the (2S,3R)-isomer (B) only in the ester residue $R^1$ until the molar ratio of ester compound (B')/(2S,3R)-isomer (B) falls within the range of 13/7 to 7.8/1, crystallizing the (2R,3S)-isomer (A) from the resulting solution containing the (2R,3S)-isomer (A), the untransesterified (2S,3R)-isomer (B) and the ester compound (B'), and isolating the (2R,3S)-isomer (A) having an optical purity of at least 99% in a yield of at least 75% based on the initial amount of (2R,3S)-isomer (A).

15. A process for preparing a (2S,3S)-isomer of a 1,5-benzothiazepine derivative of the formula (II):

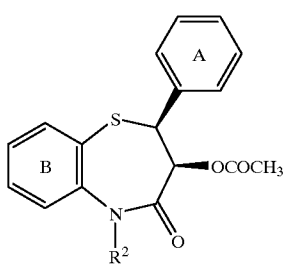

(II)

wherein ring A and ring B are independently a substituted or unsubstituted benzene ring, and R is a 2-(dimethylamino) ethyl group or a group of the formula:

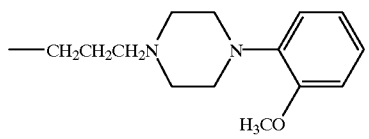

or a pharmaceutically acceptable salt thereof, which comprises (1) obtaining the (2R,3S)-isomer of a trans-3-substituted glycidic acid ester compound of the formula (I):

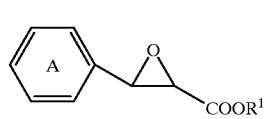

(I)

wherein ring A is a substituted or unsubstituted benzene ring, and $R^1$ is an ester residue by > subjecting a mixture of (2R,3S)-isomer (A) and (2S,3R)-isomer (B) of the ester compound (I) to transesterification in the presence of an alcohol and an enzyme having a stereoselective transesterification ability, thereby transesterifying the (2S,3R)-isomer (B) with the alcohol to produce an ester compound (B') which is different from the (2S,3R)-isomer (B) only in the ester residue $R^1$ until the molar ratio of ester compound (B')/(2S,3R)-isomer (B) falls within the range of 13/7 to 7.8/1,
>
> crystallizing the (2R,3S)-isomer (A) from the resulting solution containing the isomer (A), the unesterified (2S,3R)-isomer (B) and the ester compound (B'), and
>
> isolating the isomer (A) having an optical purity of at least 99% in a yield of at least 75% based on the initial amount of (2R,3S)-isomer (A), and (2) converting the (2R,3S)-isomer (A) to the (2S,3S)-isomer of the 1,5-benzothiazepine derivative or a pharmaceutically acceptable salt thereof.

16. The process of claim 14 or 15, wherein the enzyme has an E-value of at least 20 measured when the conversion rate of transesterification reaction is 10%.

17. The process of claim 14 or 15, wherein the enzyme is an esterase derived from *Serratia marcescens*, the molar ratio of ester compound (B')/(2S,3R)-isomer (B) is from 2/1 to 8/2, and the yield of the (2R,3S)-isomer (A) is at least 80%.

18. The process of claim 14 or 15, wherein ring A is a 4-methoxyphenyl group, the ester residue of the isomer (B) is a methyl group, and the ester residue of the ester compound (B') is a n-butyl group.

19. The process of claim 18, wherein ring B is an unsubstituted benzene ring, and $R^2$ is a 2-(dimethylamino)ethyl group.

20. In a process for preparing a (2R,3R)-1,5-benzothiazepine derivative of the formula (III):

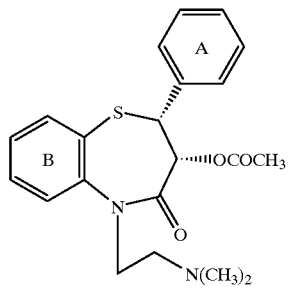

(III)

wherein ring A and ring B are independently a substituted or unsubstituted benzene ring, or a pharmaceutically acceptable salt thereof, the improvement comprising using as the starting material a (2S,3R)-isomer of a trans-3-substituted glycidic acid ester compound of the formula (I):

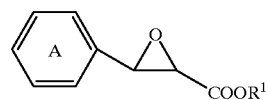

(I)

wherein ring A is a substituted or unsubstituted benzene ring, and $R^1$ is an ester residue, which is obtained by > preparing a solution of (2S,3R)-isomer (A) and (2R,3S)-isomer (B) of the ester compound (I), both of which are optical isomers due to the asymmetric carbons at the 2- and 3-positions, and an ester compound (B') which is different from the (2R,3S)-isomer (B) only in the ester residue R1,
>
> crystallizing the (2S,3R)-isomer (A) from the solution up to the extent that the (2S,3R)-isomer (A) is crystallized without the precipitation of the (2R,3S)-isomer (B) due to the presence of the ester compound (B') though the (2R,3S)-isomer (B) would precipitate if the ester compound (B') were not present, and
>
> isolating the crystals of the (2S,3R)-isomer (A).

21. A process for preparing a (2R,3R)-isomer of 1,5-benzothiazepine derivative of the formula (III):

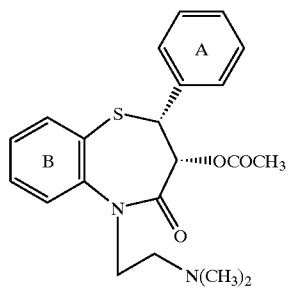

(III)

wherein ring A and ring B are independently a substituted or unsubstituted benzene ring, or a pharmaceutically acceptable salt thereof, which comprises (1) obtaining a (2S,3R)-isomer of a trans-3-substituted glycidic acid ester compound of the formula (I):

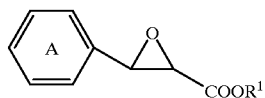

wherein ring A is a substituted or unsubstituted benzene ring, and R¹ is an ester residue by
  preparing a solution of (2S,3R)-isomer (A) and (2R,3S)-isomer (B) of the ester compound (I) and an ester compound (B') which is different from the (2R,3S)-isomer (B) only in the ester residue R¹,
  crystallizing the (2S,3R)-isomer (A) from the solution up to the extent that the (2S,3R)-isomer (A) is crystallized without the precipitation of the (2R,3S)-isomer (B) due to the presence of the ester compound (B') though the (2R,3S)-isomer (B) would precipitate if the ester compound (B') were not present, and
  isolating the crystals of the (2S,3R)-isomer (A), and
(2) converting the (2S,3R)-isomer (A) to the (2R,3R)-isomer of the 1,5-benzothiazepine derivative or a pharmaceutically acceptable salt thereof.

22. The process of claim 20 or 21, wherein the solution further contains a small amount of an ester compound (A') which is different from the (2S,3R)-isomer (A) only in the ester residue R¹ and has the same ester residue as the ester compound (B').

23. The process of claim 22, wherein the ester residue of the (2R,3S)-isomer (B) is a methyl or an ethyl group, and the ester residue of the ester compound (B') is a member selected from the group consisting of:
  (a) a linear or branched alkyl group which has more carbon atoms than that of the ester residue R¹ of the (2R,3S)-isomer (B) and which may be substituted by a halogen atom;
  (b) an alkoxyalkyl group which may be substituted by a halogen atom, and
  (c) an arylalkyl group which may be substituted by a linear or branched lower alkyl group, a linear or branched lower alkoxy group or a halogen atom.

24. The process of claim 20 or 21, wherein the molar ratio of (2S,3R)-isomer (A)/(2R,3S)-isomer (B) in the solution is from 4/6 to 10/1, and the molar ratio of ester compound (B')/(2R,3S)-isomer (B) in the solution is from 5/3 to 10/1.

25. The process of claim 22, wherein the molar ratio of ester compound (A')/(2S/3R)-isomer (A) is at most 9/35 of that of ester compound (B')/(2R,3S)-isomer (B).

26. The process of claim 20 or 21, wherein the solvent of the solution is a member selected from the group consisting of an alcohol solvent, an ether solvent, an aromatic hydrocarbon solvent which may be substituted by a halogen atom, an aliphatic hydrocarbon solvent which may be substituted by a halogen atom and an ester solvent.

27. The process of claim 20 or 21, wherein the concentration of (2S,3R)-isomer (A) in the solution prior to crystallizing is from 0.5 to 4 moles/liter, and the crystallization is carried out at a temperature of −30 to +15° C.

28. The process of claim 20 or 21, wherein the solution to be subjected to the crystallization is a solution obtained by transesterifying the (2R,3S)-isomer (B) in the solution of the (2S,3R)-isomer (A) and the (2R,3S)-isomer (B) to an ester compound (B') in the presence of an enzyme having a stereoselective transesterification ability by the use of an alcohol.

29. The process of claim 28, wherein the enzyme has an E-value of at least 20 measured when the conversion rate of transesterification reaction is 10%.

30. The process of claim 28, wherein the transesterification is conducted so that the molar ratio of ester compound (B')/(2S,3R)-isomer (B) is from 5/3 to 10/1.

31. The Process of claim 20 or 21, wherein ring A is a 4-methoxyphenyl group, ring B is an unsubstituted benzene ring, the ester residue of the (2R,3S)-isomer (B) is a methyl group, and the ester residue of the ester compound (B') is a n-butyl group.

32. In a process for preparing a (2R,3R)-1,5-benzothiazepine derivative of the formula (III):

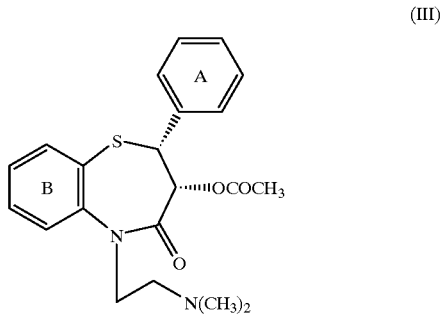

wherein ring A and ring B are independently a substituted or unsubstituted benzene ring, or a pharmaceutically acceptable salt thereof, the improvement comprising using as the starting material a (2S,3R)-isomer of a trans-3-substituted glycidic acid ester compound of the formula (I):

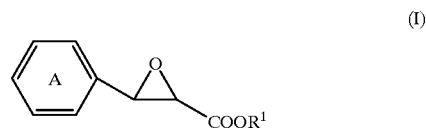

wherein ring A is a substituted or unsubstituted benzene ring, and R¹ is an ester residue, which is obtained by subjecting a mixture of (2S,3R)-isomer (A) and (2R,3S)-isomer (B) of the ester compound (I), both of which are optical isomers due to the asymmetric carbons at the 2- and 3-positions, to transesterification in the presence of an alcohol and an enzyme having a stereoselective transesterification ability, thereby transesterifying the (2R,3S)-isomer (B) with the alcohol to produce an ester compound (B') which is different from the (2R,3S)-isomer (B) only in the ester residue R¹ until the molar ratio of ester compound (B')/(2R,3S)-isomer (B) falls within the range of 13/7 to 7.8/1,
  crystallizing the (2S,3R)-isomer (A), from the resulting solution containing the (2S,3R)-isomer (A), the untransesterified (2R,3S)-isomer (B) and the ester compound (B'), and
  isolating the (2S,3R)-isomer (A) having an optical purity of at least 99% in a yield of at least 75% based on the initial amount of (2S,3R)-isomer (A).

33. A process for preparing a (2R,3R)-isomer of a 1,5-benzothiazepine derivative of the formula (III):

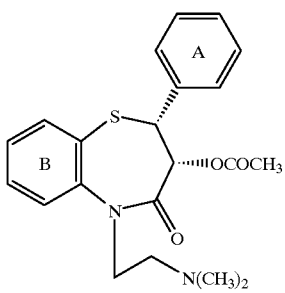

(III)

wherein ring A and ring B are independently a substituted or unsubstituted benzene ring,
or a pharmaceutically acceptable salt thereof, which comprises (1) obtaining the (2S,3R)-isomer of a trans-3-substituted glycidic acid ester compound of the formula (I):

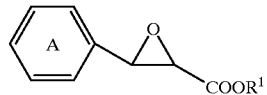

(I)

wherein ring A is a substituted or unsubstituted benzene ring, and $R^1$ is an ester residue by subjecting a mixture of (2S,3R)-isomer (A) and (2R,3S)-isomer (B) of the ester compound (I) to transesterification in the presence of an alcohol and an enzyme having a stereoselective transesterification ability, thereby transesterifying the (2R,3S)-isomer (B) with the alcohol to produce an ester compound (B') which is different from the (2R,3S)-isomer (B) only in the ester residue $R^1$ until the molar ratio of ester compound (B')/(2R,3S)-isomer (B) falls within the range of 13/7 to 7.8/1, crystallizing the (2S,3R)-isomer (A) from the resulting solution containing the isomer (A), the unesterified (2R,3S)-isomer (B) and the ester compound (B'), and isolating the isomer (A) having an optical purity of at least 99% in a yield of at least 75% based on the initial amount of (2S,3R)-isomer (A), and (2) converting the (2S,3R)-isomer (A) to the (2S,3R)-isomer of the 1,5-benzothiazepine derivative or a pharmaceutically acceptable salt thereof.

34. The process of claim 32 or 33, wherein the enzyme has an E-value of at least 20 measured when the conversion rate of transesterification reaction is 10%.

35. The process claim 32 or 33, wherein ring A is a 4-methoxyphenyl group, ring B is an unsubstituted benzene ring, the ester residue of the isomer (B) is a methyl group, and the ester residue of the ester compound (B') is a n-butyl group.

* * * * *